(12) United States Patent
Spicer et al.

(10) Patent No.: US 11,498,834 B1
(45) Date of Patent: Nov. 15, 2022

(54) PRODUCTION OF HYDROGEN-RICH FUEL-GAS WITH REDUCED $CO_2$ EMISSION

(71) Applicant: ExxonMobil Chemical Patents Inc., Baytown, TX (US)

(72) Inventors: David Spicer, Houston, TX (US); Thomas T. Hirst, Houston, TX (US); James L. Kendall, Humble, TX (US); You Fang, Singapore (SG)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/483,939

(22) Filed: Sep. 24, 2021

(51) Int. Cl.
  *C01B 3/38* (2006.01)
  *C07C 4/02* (2006.01)

(52) U.S. Cl.
  CPC ............ *C01B 3/38* (2013.01); *C07C 4/025* (2013.01); *C01B 2203/1241* (2013.01); *C01B 2203/84* (2013.01)

(58) Field of Classification Search
  CPC ............ C01B 3/38; C01B 2203/12441; C01B 2203/84; C07C 4/025
  See application file for complete search history.

(56) References Cited

U.S. PATENT DOCUMENTS

| | | | |
|---|---|---|---|
| 4,869,894 | A | 9/1989 | Wang et al. |
| 8,021,464 | B2 | 9/2011 | Gauthier et al. |
| 8,460,630 | B2 | 6/2013 | Niitsuma et al. |
| 9,216,903 | B2 | 12/2015 | McKenna et al. |

(Continued)

FOREIGN PATENT DOCUMENTS

WO    2020/131981    6/2020

OTHER PUBLICATIONS

U.S. Appl. No. 17/483,960, filed Sep. 24, 2021, Entitled "Hydrocarbon Reforming Processes with Shaft Power Production" Spicer.
U.S. Appl. No. 17/484,042, filed Sep. 24, 2021, Entitled "Integration of Hydrogen-Rich Fuel-Gas Production with Olefins Production Plant" Spicer et al.

(Continued)

*Primary Examiner* — Thuan D Dang
(74) *Attorney, Agent, or Firm* — ExxonMobil Chemical Patents Inc.; Siwen Chen

(57) ABSTRACT

An $H_2$-rich fuel gas stream can be advantageously produced by reforming a hydrocarbon/steam mixture in to produce a reformed stream, followed by cooling the reformed stream in a waste-heat recovery unit to produce a high-pressure steam stream, shifting the cooled reformed stream a first shifted stream, cooling the first shifted stream, shifting the cooled first shifted stream to produce a second shifted stream, cooling the second shifted stream, abating water from the cooled second shifted stream to obtain a crude gas mixture stream comprising $H_2$ and $CO_2$, and recovering a $CO_2$ stream from the crude gas mixture stream. The $H_2$-rich stream can be advantageously combusted to provide thermal energy needed for residential, office, and/or industrial applications including in the $H_2$-rich fuel gas production process. The $H_2$-rich fuel gas production process can be advantageously integrated with an olefins production plant comprising a steam cracker.

25 Claims, 3 Drawing Sheets

(56) References Cited

U.S. PATENT DOCUMENTS

| | | |
|---|---|---|
| 9,580,314 B2 | 2/2017 | Darde et al. |
| 11,021,365 B2 | 6/2021 | Van Willigenburg |
| 2009/0117024 A1 | 5/2009 | Weedon et al. |
| 2010/0126180 A1 | 5/2010 | Forsyth et al. |
| 2010/0176346 A1* | 7/2010 | Musich .................. B01J 8/025 |
| | | 252/373 |

OTHER PUBLICATIONS

U.S. Appl. No. 17/484,068, filed Sep. 24, 2021, Entitled "Amine CO2 Separation Process Integrated with Hydrocarbons Processing" Spicer et al.
IEAGHG Technical Review 2017-TR3 Mar. 2017 Reference Data and Supporting Literature Reviews for SMR Based Hydrogen Production with Ccs, Iea Greenhouse Gas R&D Programme, 131 pages.
IEAGHG, "Techno-Economic Evaluation of SMR Based Stand-alone (Merchant) Plant with CCS", Feb. 2017, Feb. 2017, 286 pages.
Ullman's Encyclopedia of Industrial Chemistry, vol. 18, 2012, "Hydrogen, 2. Production" pp. 258-268.
"The Petra Nova Carbon Capture Project" MHI Brochure # ZD01-003C02E2-A-1, 2 pages.

* cited by examiner

PRODUCTION OF HYDROGEN-RICH FUEL-GAS WITH REDUCED $CO_2$ EMISSION

FIELD

This disclosure relates to processes for producing $H_2$-rich fuel gas from hydrocarbons such as natural gas, and use thereof in heating such as industrial heating in an olefins production plant.

BACKGROUND

There exist many industrial processes that require the generation of very high temperatures. Many of these processes achieve the required high temperatures by the combustion of hydrocarbon fuel-gas. A fuel-gas commonly used is natural gas, which comprises primarily methane. In the combustion of methane, approximately 5.8 tons of $CO_2$ are generated for each 100 MBtu of heat released (lower heating value ("LHV" basis).

One such large scale manufacturing process is the production of light olefins (e.g. ethylene, propylene, etc.). The predominant method of manufacturing light olefins is via steam-cracking, where a hydrocarbon feed is heated to very high temperatures in the presence of steam. The high temperatures (>2100° F.) required to provide rapid heat input to steam-cracking furnaces (also known as pyrolysis reactors) are achieved by the combustion of fuel-gas. In many olefins production facilities the fuel-gas is internally generated as a byproduct of the cracking process, which can comprise primarily methane (e.g., 70-90 mol %) with a moderate hydrogen content (e.g., 10-30 mol %). A modern, world-scale olefins plant may have up to 10 steam-cracking furnaces, each of which may consume up to 150 MW or 512 MBtu/hour of fuel (LHV basis), and each of which has an individual flue-gas exhaust stack. Thus a modern olefins production facility can generate considerable quantity of $CO_2$ emissions over an extended operation period.

Various techniques have been proposed to reduce the net $CO_2$ emissions from steam cracking furnaces and olefins plants. Capturing $CO_2$ from the individual flue-gas stacks using an amine absorption and regeneration process has been proposed. This process has been demonstrated on the flue-gas stacks of electricity generation facilities. Once captured from the flue-gas stack, the $CO_2$ can be compressed, liquefied and can be sequestered in appropriate geological formations (i.e., Carbon Capture and Sequestration, "CCS"). Application of this technology to an olefins plant is extremely expensive given the potential to have 10 (or more) flue-gas stacks from which $CO_2$ must be captured, the low $CO_2$ concentration in the flue-gas, and the lack of available plot-space close to the steam-cracking furnaces in existing facilities. In particular, the large, internally insulated flue-gas ducting, with associated fans and isolation facilities required to transfer the large flue-gas volumes from the furnaces to the location of the amine absorption unit greatly increases the cost of the facilities.

An alternative approach has been proposed wherein a high-hydrogen fuel-gas stream is generated for combustion in the steam-cracking furnaces, thus facilitating the generation of the high temperatures required by the process but with appreciably reduced $CO_2$ emissions from the furnaces.

Hydrogen generation from natural-gas is practiced on an industrial scale via the process of steam reforming. A steam-methane reformer passes heated natural-gas (or another suitable hydrocarbon), in the presence of large volumes of steam, through tubes containing a suitable catalyst, to produce a synthesis gas containing hydrogen, carbon-monoxide, carbon-dioxide and unconverted methane. The process is typically practiced at pressures in the range of 300-400 psig. The process requires high temperatures, so it is normal for various waste-heat recovery heat exchangers to be employed in the reformer effluent stream. The waste heat recovery exchangers typically generate high-pressure steam 600-650 psig) which is then superheated in the convection section of the reformer. Also in the reformer effluent stream, located at appropriate temperature conditions, it is normal to employ one or more "shift reactors" where, over a suitable catalyst, CO reacts with steam to produce additional hydrogen and $CO_2$. Following the shift reactor(s), the reformer effluent is further cooled to condense the contained steam, leaving a stream predominantly containing hydrogen and $CO_2$, but also containing unconverted methane and CO. In most industrial facilities a pressure-swing-absorption ("PSA") unit is then employed to recover high purity hydrogen (99+%) from the effluent stream. A so-called "PSA reject" stream is also generated, composed of $CO_2$, CO, unconverted methane and some hydrogen. Historically it has been normal to use the PSA reject stream as a portion of the fuel-requirement of the reformer.

While the steam-methane-reforming process for hydrogen production is well established, there remain several drawbacks to its use for large scale production of hydrogen rich fuel-gas for industrial applications. First, from the description above, it is clear that the process has a high capital cost, employing large reforming furnaces and multiple subsequent processing steps. Second, the combustion of fuel-gas to provide the high temperatures required in the reformer itself can be source of considerable amount of $CO_2$ emissions. Third, the PSA reject stream must be sent to a suitable disposition. Historically the PSA reject stream formed part of the fuel-gas supply to the reformer, but this further adds to the $CO_2$ emissions from the reformer itself.

The $CO_2$ emissions from the SMR can be reduced by installing an amine recovery system on the flue-gas discharged from the reformer stack. This approach further adds to the capital cost and operating expense of the system, particularly as the reformer stack gas is at low (ambient) pressure. The low operating pressure translates to large gas volumes and hence the amine contactor required to absorb the $CO_2$ becomes extremely large.

There is a need, therefore, for improved processes and systems for producing $H_2$-rich fuel gas and processes and systems for producing olefins. This disclosure satisfies this and other needs.

SUMMARY

It has been found that, in a surprising manner, a $H_2$-rich fuel gas can be produced with a considerably improved efficiency compared to existing processes by a process comprising hydrocarbon reforming with waste heat recovery, at least two stages of shift reactions, and a $CO_2$ separation step. The $H_2$-rich fuel gas stream can be advantageously supplied as fuel to furnaces such as a SMR furnace, a pre-reformer furnace, and to boilers. The separated $CO_2$ can be conducted away, stored, sequestered, or utilized, enabling the production of the $H_2$-rich fuel gas with considerably reduced $CO_2$ emission to the atmosphere. The $H_2$-rich fuel gas can be advantageously integrated with an olefins production plant achieving additional, considerably improved energy efficiency and appreciably reduced $CO_2$ emissions from the olefins production plant compared to running the olefins production plant separately.

Thus, a first aspect of this disclosure is directed to a process comprising one or more of the following steps: (I) supplying a hydrocarbon feed and a steam feed into a syngas producing unit comprising a reforming reactor under syngas producing conditions to produce a reformed stream exiting the reforming reactor, wherein the syngas producing conditions include the presence of a reforming catalyst, and the reformed stream comprises $H_2$, CO, and steam; (II) cooling the reformed stream by using a waste heat recovery unit ("WHRU") to produce a cooled reformed stream and to generate a high-pressure steam ("HPS") stream; (III) contacting the cooled reformed stream with a first shifting catalyst in a first shift reactor under a first set of shifting conditions to produce a first shifted stream exiting the first shift reactor, wherein the first shifted stream has a lower CO concentration and a higher $CO_2$ concentration than the cooled reformed stream; (IV) cooling the first shifted stream to obtain a cooled first shifted stream; (V) contacting the cooled first shifted stream with a second shifting catalyst in a second shift reactor under a second set of shifting conditions to produce a second shifted stream exiting the second shift reactor, wherein the second shifted stream has a lower CO concentration and a higher $CO_2$ concentration than the cooled first shifted stream; (VI) abating steam present in the second shifted stream to produce a crude gas mixture stream comprising $CO_2$ and $H_2$; (VII) recovering at least a portion of the $CO_2$ present in the crude gas mixture stream to produce a $CO_2$ stream and a $H_2$-rich stream, wherein the $H_2$-rich stream comprises $H_2$ at a concentration of at least 80 mol %, based on the total moles of molecules in the $H_2$-rich stream; (VIII) combusting a portion of the $H_2$-rich stream in the presence of an oxidant to generate thermal energy and to produce a flue gas stream; and (IX) operating a steam cracker located in an olefins production plant under steam cracking conditions to convert a steam cracker feed into a steam cracker effluent comprising olefins; (X) producing a CH4-rich stream from the steam cracker effluent; and (XI) providing the CH4-rich stream as at least a portion of the hydrocarbon feed in step (I).

DETAILED DESCRIPTION

Figure 1:
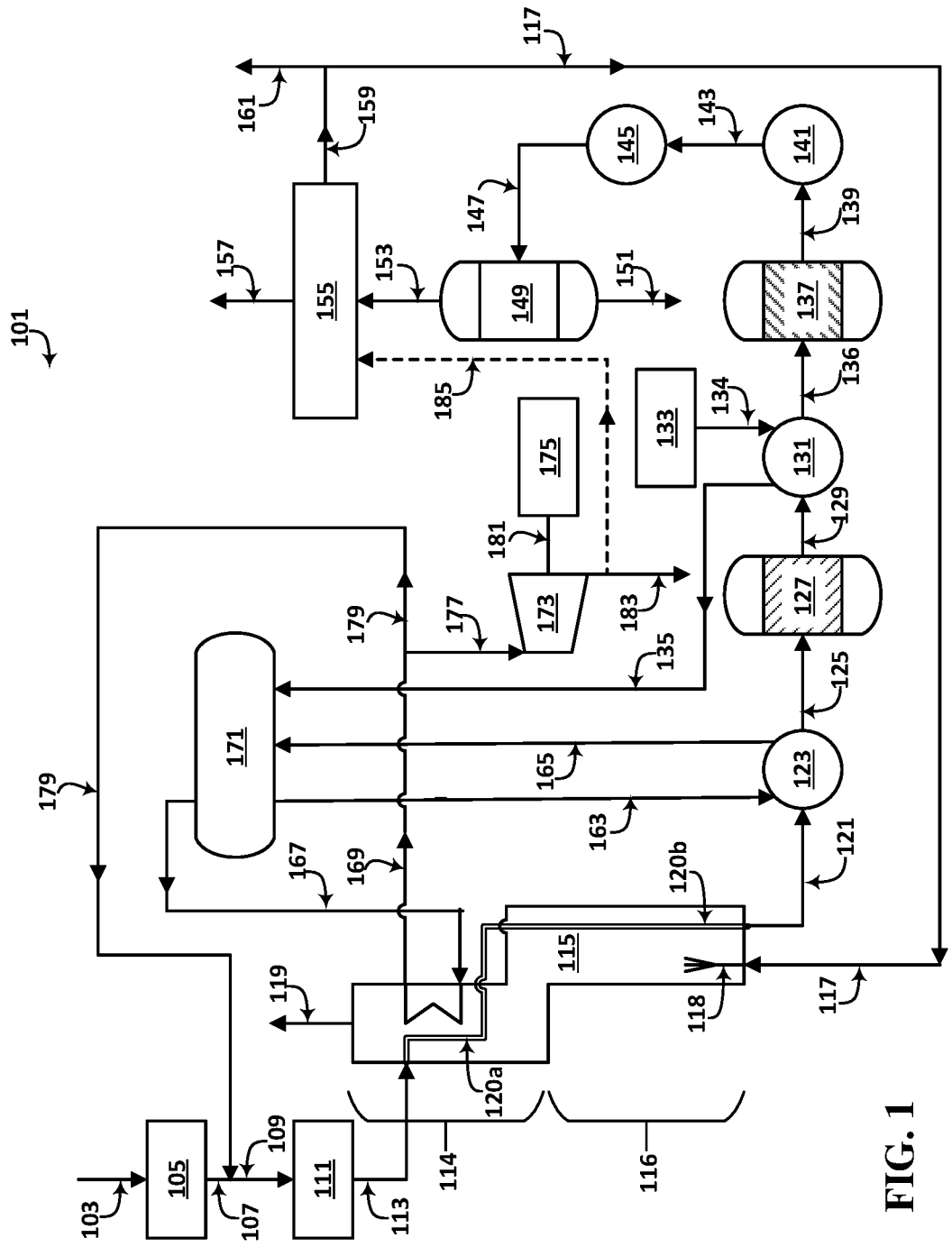
FIG. 1 schematically illustrates certain processes and systems for producing a $H_2$-rich stream including an SMR according to certain embodiments of this disclosure.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16th Ed., John Wiley & Sons, Inc., (2016), Appendix V.

"High-pressure steam" and "HPS" are used interchangeably to mean a steam having an absolute pressure of at least 4000 kilopascal ("kPa"). "Super-high-pressure steam" and "Super-HPS" are used interchangeably to mean a steam having an absolute pressure of at least 8,370 kPa. Thus, a Super-HPS is an HPS. "Medium-pressure steam" and "MPS" are used interchangeably to mean a steam having an absolute pressure of at least 800 kPa but less than 4,000 kPa. "Low-pressure steam" and "LPS" are used interchangeably to mean a steam having an absolute pressure of at least 200 kPa but less than 800 kPa.

"Consisting essentially of" means comprising ≥60 mol %, preferably ≥75 mol %, preferably ≥80 mol %, preferably ≥90 mol %, preferably ≥95 mol %; preferably 98 mol %, of a given material or compound, in a stream or mixture, based on the total moles of molecules in the stream or mixture.

The Plant and Process for Producing a $H_2$-Rich Fuel Gas

A first aspect of this disclosure is directed to a process for producing $H_2$-rich fuel gas as summarily above. A system for producing such an $H_2$-rich stream, preferably using a process including steps (I) to (VII) as described summarily above, may be called an $H_2$-rich fuel gas production plant in this disclosure. Step (I) of this process includes supplying a hydrocarbon feed and a steam feed into a syngas producing unit comprising a reforming reactor under syngas producing conditions to produce a reformed stream exiting the reforming reactor, wherein the syngas producing conditions include the presence of a reforming catalyst, and the reformed stream comprises $H_2$, CO, and steam. The hydrocarbon feed can consist essentially of C1-C4 hydrocarbons (preferably saturated), preferably consists essentially of C1-C3 hydrocarbons (preferably saturated), preferably consists essentially of C1-C2 hydrocarbons (preferably saturated), and preferably consists essentially of $CH_4$. The hydrocarbon feed and the steam feed may be combined to form a joint stream before being fed into the syngas producing unit.

Alternatively, they may be fed into the syngas producing unit as separate streams, in which they admix with each other to form a mixture. The feed stream(s) can be pre-heated by, e.g., a furnace, a heat exchanger, and the like, before being fed into the syngas producing unit. The syngas producing unit can comprise a pre-reformer first receiving the feed stream(s), especially if the hydrocarbon feed comprises significant amount of C2+ hydrocarbons. In a pre-reformer, the hydrocarbon feed/steam feed mixture contacts a pre-reforming catalyst under conditions such that the C2+ hydrocarbons are preferentially converted into $CH_4$. The inclusion of a pre-reformer can reduce coking and fouling of the down-stream reforming reactor. The hydrocarbon feed may have a temperature from, e.g., 15° C., 20° C., 30° C., 40° C., to 50° C., 60° C., 70° C., 80° C., 90° C., to 95° C., 100° C., 110° C., 120° C., 130° C., 140° C., or even 150° C., and an absolute pressure from e.g., 1,300 kPa, 1,400 kPa, 1,500 kPa, 1,600 kPa, 1,700 kPa, 1,800 kPa, 1,900 kPa, 2,000 kPa, to 2,100 kPa, 2,200 kPa, 2,300 kPa, 2,400 kPa, 2,500 kPa, 2,600 kPa, 2,700 kPa, 2,800 kPa, 2,900 kPa, 3,000 kPa, to 3,000 kPa, 3,200 kPa, 3,400 kPa, 3,500 kPa, 3,600 kPa, 3,800 kPa, 4,000 kPa, to 4,200 kPa, 4,400 kPa, 4,500 kPa, 4,600 kPa, 4,800 kPa, or even 5,000 kPa. The steam feed may have a temperature from, e.g., 250° C., 260° C., 270° C., 280° C., 290° C., 300° C., to 310° C., 320° C., 330° C., 340° C., 350° C., 360° C., 370° C., 380° C., 390° C., to 400° C., 410° C., 420° C., 430° C., 440° C., or even 450° C., and an absolute pressure from e.g., 1,300 kPa, 1,400 kPa, 1,500 kPa, 1,600 kPa, 1,700 kPa, 1,800 kPa, 1,900 kPa, 2,000 kPa, to 2,100 kPa, 2,200 kPa, 2,300 kPa, 2,400 kPa, 2,500 kPa, 2,600 kPa, 2,700 kPa, 2,800 kPa, 2,900 kPa, 3,000 kPa, to 3,000 kPa, 3,200 kPa, 3,400 kPa, 3,500 kPa, 3,600 kPa, 3,800 kPa, 4,000 kPa, to 4,200 kPa, 4,400 kPa, 4,500 kPa, 4,600 kPa, 4,800 kPa, or even 5,000 kPa. Preferably, the steam feed is a superheated steam.

The effluent from the pre-reformer can be then fed into the reforming reactor operated under syngas producing conditions, wherein the forward reaction of the following is favored and desirably occurs in the presence of the reforming catalyst:

$$CH_4 + H_2O \xrightleftharpoons{\text{Reforming Catalyst}} CO + 3 H_2 \quad \text{(R-1)}$$

The syngas producing condition can include a temperature of, e.g., from 750° C., 760° C., 780° C., 800° C., 850° C., 900° C., to 950° C., 1,000° C., 1,050° C., 1,100° C., to 1150° C., or even 1200° C., and an absolute pressure of, e.g., from 700 kPa, 800 kPa, 900 kPa, 1,000 kPa, to 1,500 kPa, 2,000 kPa, 2,500 kPa, 3,000 kPa, to 3,500 kPa, 4,000 kPa, 4,500 kPa, or even 5,000 kPa, in the reforming reactor, depending on the type of the reforming reactor and the syngas producing conditions. A lower pressure in the reformed stream, and hence a lower pressure in the reforming reactor, is conducive to a higher conversion of $CH_4$ in reforming reactor and hence a lower residual $CH_4$ concentration in the reformed stream. The reformed stream exiting the reforming reactor therefore comprises CO, $H_2$, residual $CH_4$ and $H_2O$, and optionally $CO_2$ at various concentrations depending on, among others, the type of the reforming reactor and the syngas producing conditions. The reformed stream can have a temperature of, e.g., from 750° C., 760° C., 780° C., 800° C., 850° C., 900° C., to 950° C., 1,000° C., 1,050° C., 1,100° C., to 1150° C., or even 1200° C., and an absolute pressure of, e.g., from 700 kPa, 800 kPa, 900 kPa, 1,000 kPa, to 1,500 kPa, 2,000 kPa, 2,500 kPa, 3,000 kPa, to 3,500 kPa, 4,000 kPa, 4,500 kPa, or even 5,000 kPa, depending on the type of the reforming reactor and the syngas producing conditions.

A preferred type of the reforming reactor in the syngas producing unit is an SMR. An SMR typically comprises one or more heated reforming tubes containing the reforming catalyst inside. The hydrocarbon/steam feed stream enters the tubes, heated to a desired elevated temperature, and passes through the reforming catalyst to effect the desirable reforming reaction mentioned above. While an SMR can have many different designs, a preferred SMR comprises a furnace enclosure, a convection section (e.g., an upper convection section), a radiant section (e.g., a lower radiant section), and one or more burners located in the radiant section combusting a fuel to produce a hot flue gas and supply thermal energy to heat the radiant section and the convection section. The hydrocarbon/steam feed stream enters the reforming tube at a location in the convection section, winds downwards through the convection section, whereby it is pre-heated by the ascending hot flue gas produced from fuel combustion at the burner(s), and then enters the radiant section proximate the burners combustion flames, whereby it contacts the reforming catalyst loaded in the reforming tube(s) in the radiant section, to produce a reformed stream exiting the SMR from a location in the radiant section. The syngas producing conditions in the reforming tube(s) in the radiant section can include a temperature of, e.g., from 750° C., 760° C., 780° C., 800° C., to 820° C., 840° C., 850° C., to 860° C., 880° C., or even 900° C., and an absolute pressure of, e.g., from 700 kPa, 800 kPa, 800 kPa, 900 kPa, 1,000 kPa, to 1,500 kPa, 2,000 kPa, 2,500 kPa, 3,000 kPa, or even 3,500 kPa. To achieve a high $CH_4$ conversion in the SMR, and a low $CH_4$ concentration in the $H_2$-rich stream produced from the process, the syngas producing conditions in the SMR preferably includes an absolute pressure of ≤2,169 kPa (300 psig), more preferably ≤1,825 kPa (250 psig). Description of an SMR can be found in, e.g., The International Energy Agency Greenhouse Gas R&D Program ("IEAGHG"), "Techno-Economic Evaluation of SMR Based Standalone (Merchant) Plant with CCS", February 2017; and IEAGHG, "Reference data and supporting literature Reviews for SMR based Hydrogen production with CCS", 2017-TR3, March 2017, the contents of which are incorporated herein in their entirety.

The reforming reactor in the syngas producing unit may comprise an autothermal reformer ("ATR"). An ATR typically receives the hydrocarbon/steam feed(s) and an $O_2$ stream into a reaction vessel, where a portion of the hydrocarbon combusts to produce thermal energy, whereby the mixture is heated to an elevated temperature and then allowed to contact a bed of reforming catalyst to effect the desirable reforming reaction and produce a reformed stream exiting the vessel. An ATR can be operated at a higher temperature and pressure than an SMR. The syngas producing conditions in the ATR and the reformed stream exiting an ATR can have a temperature of, e.g., from 800° C., 850° C., 900° C., to 950° C., 1,000° C., 1050° C., to 1,100° C., 1,150° C., or even 1,200° C., and an absolute pressure of, e.g., from 800 kPa, 900 kPa, 1,000 kPa, to 1,500 kPa, 2,000 kPa, 2,500 kPa, 3,000 kPa, to 3,500 kPa, 4,000 kPa, 4,500 kPa, or even 5,000 kPa. Commercially available ATRs, such as the Syncor™ ATR available from Haldor Topsoe, having an address at Haldor Topsøes Allé 1, DK-2800, Kgs. Lyngby, Denmark ("Topsoe"), may be used in the process of this disclosure.

The syngas producing unit used in step (I) of the process of this disclosure can include one or more SMR only, one or more ATR only, or a combination of one or more of both.

The reformed stream exiting the reforming reactor has a high temperature and high pressure as indicated above. It is highly desirable to capture the heat energy contained therein. Thus, in step (II), the reformed stream passes through a waste heat recovery unit ("WHRU") to produce a cooled reformed stream and to generate a high-pressure steam ("HPS") stream. The cooled reformed stream can have a temperature from, e.g., 285° C., 290° C., 300° C., to 310° C., 320° C., 330° C., 340° C., 350° C., to 360° C., 370° C., 380° C., 390° C., or even 400° C. The cooled reformed stream can have a pressure substantially the same as the reformed stream exiting the reforming reactor. The WHRU can include, e.g., one or more heat exchanger and one or more steam drum in fluid communication with the heat exchanger. The steam drum supplies a water/steam stream to the heat exchanger, where it is heated and can be then returned to the steam drum, where steam is separated from liquid phase water. The HPS stream can have an absolute pressure from, e.g., 4,000 kPa, 5,000 kPa, 6,000 kPa, 7,000 kPa, 8,000 kPa, to 9,000 kPa, 10,000 kPa, 11,000 kPa, 12,000 kPa, 13,000 kPa, or even 14,000 kPa. The thus produced HPS stream is a saturated steam stream. To make the HPS stream more useful, it may be further heated to produce a superheated HPS ("SH-HPS") stream in, e.g., a furnace. In case the syngas producing unit comprises an SMR having a convection section as described above, the saturated HPS stream may be advantageously superheated in the convection section of the SMR and/or in an auxiliary furnace. In case the syngas producing unit comprises one or more ATR but no SMR, the saturated HPS stream can be superheated in an auxiliary furnace. The auxiliary furnace can include one or more burners combusting a fuel gas stream to supply the needed thermal energy as is known to one skilled in the art. The SH-HPS stream can have one of both of: (i) a temperature from, e.g., 350° C., 360° C., 370° C., 380° C., 390° C., 400° C., to 410° C., 420° C., 430° C., 440° C., 450° C., to 460° C., 470° C., 480° C., 490° C., 500° C., to 510° C., 520° C., 530° C., 540° C., or even 550° C.; and (ii) an absolute pressure from, e.g., e.g., 4,000 kPa, 5,000 kPa, 6,000 kPa, 7,000 kPa, 8,000 kPa, to 9,000 kPa, 10,000 kPa, 11,000 kPa, 12,000 kPa, 13,000 kPa, or even 14,000 kPa.

In step (III) of the process of this disclosure, the cooled reformed stream contacts a first shifting catalyst in a first shift reactor under a first set of shifting conditions to produce a first shifted stream exiting the first shift reactor. The first set of shifting conditions includes the presence of a first shift catalyst. Any suitable shift catalyst known to one skilled in the art may be used. Non-limiting examples of suitable shift catalyst for the first shifting catalyst are high temperature shift catalysts available from, e.g., Topsoe. The forward reaction of the following preferentially occur in the first shift reactor:

(R-2)

$$CO + H_2O \xrightleftharpoons{\text{First Shift Catalyst}} CO_2 + H_2$$

As such, the first shifted stream has a lower CO concentration and a higher $CO_2$ concentration than the cooled reformed stream. The forward reaction of (R-2) is exothermic, resulting in the first shifted stream having a temperature higher than the cooled reformed stream entering the first shift reactor. The first shifted stream exiting the first shift reactor can have a temperature from, e.g., 335° C., 340° C., 350° C., 360° C., to 370° C., 380° C., 400° C., 420° C., to 440° C., 450° C., 460° C., 480° C., or even 500° C. The first shifted stream can have an absolute pressure substantially the same as the cooled reformed stream.

While a single stage of shift reactor may convert sufficient amount of CO in the cooled reformed stream to $CO_2$ resulting in a low CO concentration in the first shifted stream, it is preferable to include at least two stages of shift reactors in the processes of this disclosure to achieve a high level of conversion of CO to $CO_2$, and eventually to produce a $H_2$-rich fuel gas stream with low CO concentration. It is further preferred that a subsequent stage, such as the second shift reactor downstream of the first shift reactor is operated at a temperature lower than the first shift reactor, whereby additional amount of CO in the first shifted stream is further converted into $CO_2$ and additional amount of $H_2$ is produced. To that end, the first shifted stream is preferably first cooled down in step (IV) to produce a cooled first shifted stream.

Such cooling can be effected by one or more heat exchangers using one or more cooling streams having a temperature lower than the first shifted stream. In one preferred embodiment, the first shifted stream can be cooled by the hydrocarbon stream or a split stream thereof to be fed into the syngas producing unit. Alternatively or additionally, the first shifted stream can be cooled by a boiler water feed stream to produce a heated boiler water stream, a steam stream, and/or a water/steam mixture stream. The thus heated boiler water stream can be heated in a boiler to produce steam at various pressure. The thus heated boiler water stream or steam stream can be further heated by another process stream in another heat exchanger to produce steam. In one preferred embodiment, the heated boiler water stream and/or steam stream can be fed into the steam drum of the WHRU extracting heat from the reformed stream as described above, where the boiler feedwater can be sent to the WHRU exchanger for further heating, and any steam separated in the steam drum can be further superheated. The cooled first shifted stream can have a temperature from, e.g., 150° C., 160° C., 170° C., 180° C., 190° C., 200° C., to 210° C., 220° C., 230° C., 240° C., or even 250° C., and a pressure substantially the same as the first shifted stream.

The cooled first shifted stream is then subjected to a low-temperature shifting in a second shift reactor under a second set of shifting conditions to produce a second shifted stream. The second set of shifting conditions includes the presence of a second shift catalyst, which may be the same or different from the first shift catalyst. Any suitable shift catalyst known to one skilled in the art may be used. Non-limiting examples of suitable catalyst for the second shifting catalyst are low temperature shift catalysts available from, e.g., Topsoe. The forward reaction of the following preferentially occur in the second shift reactor:

(R-3)

As such, the second shifted stream has a lower CO concentration and a higher $CO_2$ concentration than the cooled first shifted stream. The forward reaction of (R-3) is exothermic, resulting in the second shifted stream having a temperature higher than the cooled first shifted stream entering the second shift reactor. The second shifted stream exiting the second shift reactor can have a temperature from, e.g., e.g., 150° C., 160° C., 170° C., 180° C., 190° C., 200° C., to 210° C., 220° C., 230° C., 240° C., 250° C., to 260° C., 270° C., 280° C., 290° C., or even 300° C. The second shifted stream can have an absolute pressure substantially the same as the cooled first shifted stream.

The second shifted stream comprises $H_2$, $CO_2$, CO, steam, and optionally $CH_4$. In step (VI), steam is then abated from it by cooling and separation. Similar to step (IV) of cooling the first shifted stream, such cooling of the second shifted stream can be effected by one or more heat exchangers using one or more cooling streams having a temperature lower than the second shifted stream. In one preferred embodiment, the second shifted stream can be cooled by the hydrocarbon stream or a split stream thereof to be fed into the syngas producing unit. Alternatively or additionally, the second shifted stream can be cooled by a boiler water feed stream to produce a heated boiler water stream, a steam stream, and/or a water/steam mixture stream. The thus heated boiler water stream and/or water/steam mixture stream can be heated in a boiler to produce steam at various pressure. The thus heated boiler water stream can be heated in a boiler to produce steam at various pressure. The thus heated boiler water stream or steam stream can be further heated by another process stream in another heat exchanger to produce steam. In one preferred embodiment, the heated boiler water stream and/or steam stream can be fed into the steam drum of the WHRU extracting heat from the reformed stream as described above, where the boiler feedwater can be sent to the WHRU exchanger for further heating, and any steam separated in the steam drum can be further superheated. Alternatively or additionally, cooling water exchangers or air-fin heat exchangers can be used to at least partly cool the second shifted syngas stream. The cooled second shifted stream can preferably comprise water condensate, which can be separated to produce a crude gas mixture stream comprising steam at a significantly lower concentration than the second shifted stream exiting the second shift reactor.

The crude gas mixture stream thus consists essentially of $CO_2$, $H_2$, optionally $CH_4$ at various amounts, and steam and CO as minor components. The crude gas mixture stream can have an absolute pressure from, e.g., 700 kPa, 800 kPa, 800 kPa, 900 kPa, 1,000 kPa, to 1,500 kPa, 2,000 kPa, 2,500 kPa, 3,000 kPa, to 3,500 kPa, 4,000 kPa, 4,500 kPa, or even 5,000 kPa. In step (VII), one can recover a portion of the $CO_2$ therein to produce a $CO_2$ stream and a $H_2$-rich stream. Any suitable $CO_2$ recovery process known to one skilled in the art may be used in step (VII), including but not limited to: (i) amine absorption and regeneration process; (ii) a cryogenic $CO_2$ separation process; (iii) a membrane separation process; (iv) a physical absorption and regeneration process; and (iv) any combination any of (i), (ii), and (iii) above. In a preferred embodiment, an amine absorption and regeneration process may be used. Due to the elevated pressure of the crude gas mixture stream, the size of the $CO_2$ recovery equipment can be much smaller than otherwise required to recover $CO_2$ from a gas mixture at atmospheric pressure.

The $CO_2$ stream preferably comprises $CO_2$ at a molar concentration of from, e.g., 90%, 91%, 92%, 93%, 94%, to 95%, 96%, 97%, 98%, or even 99%, based on the total moles of molecules in the $CO_2$ stream. The $CO_2$ stream can comprise at least one and preferably all of, on a molar basis: (i) e.g., from 0.1%, 0.2%, 0.3%, 0.4%, 0.5%, 0.6%, 0.7%, 0.8%, 0.9%, to 1.0%, 1.5%, 2.0%, 2.5%, 3.0%, 3.5%, 4.5%, or even 5.0% of CO; (ii) e.g., from 0.1%, 0.2%, 0.3%, 0.4%, 0.5%, 0.6%, 0.7%, 0.8%, 0.9%, to 1.0%, 1.5%, 2.0%, 2.5%, 3.0%, 3.5%, 4.5%, 5.0%, 5.5%, or even 6.0% of $H_2O$; and (iii) e.g., from 0.1%, 0.2%, 0.3%, 0.4%, 0.5%, 0.6%, 0.7%, 0.8%, 0.9%, to 1.0%, 1.5%, 2.0%, 2.5%, 3.0%, 3.5%, 4.5%, or even 5.0% of $CH_4$. The $CO_2$ stream can have an absolute pressure from, e.g., 700 kPa, 800 kPa, 800 kPa, 900 kPa, 1,000 kPa, to 1,500 kPa, 2,000 kPa, 2,500 kPa, 3,000 kPa, to 3,500 kPa, 4,000 kPa, 4,500 kPa, or even 5,000 kPa. The $CO_2$ stream can be compressed, liquefied, conducted away, stored, sequestered, or utilized in any suitable applications known to one skilled in the art. In one embodiment, the $CO_2$ stream, upon optional compression, can be conducted away in a $CO_2$ pipeline. In another embodiment, the $CO_2$ stream, upon optional compression and/or liquefaction, can be injected and stored in a geological formation. In yet another embodiment, the $CO_2$ stream, upon optional compression and/or liquefaction, can be used in extracting hydrocarbons present in a geological formation. Another exemplary use of the $CO_2$ stream is in food applications.

The $H_2$-rich stream can have an absolute pressure from, e.g., 700 kPa, 800 kPa, 800 kPa, 900 kPa, 1,000 kPa, to 1,500 kPa, 2,000 kPa, 2,500 kPa, 3,000 kPa, to 3,500 kPa, 4,000 kPa, 4,500 kPa, or even 5,000 kPa. The $H_2$-rich stream preferably comprises $H_2$ at a molar concentration of from, e.g., 80%, 81%, 82%, 83%, 84%, 85%, to 86%, 87%, 88%, 89%, 90%, to 91%, 92%, 93%, 94%, 95%, to 96%, 97%, or even 98%, based on the total moles of molecules in the $H_2$-rich stream. The $H_2$-rich stream can comprise at least one and preferably all of, on a molar basis: (i) e.g., from 0.1%, 0.2%, 0.3%, 0.4%, 0.5%, 0.6%, 0.7%, 0.8%, 0.9%, to 1.0%, 1.5%, 2.0%, 2.5%, or even 3.0%, of CO; (ii) e.g., from 0.1%, 0.2%, 0.3%, 0.4%, 0.5%, to 0.6%, 0.7%, 0.8%, 0.9%, or even 1.0%, of $CO_2$; and (iii) e.g., from 0.1%, 0.2%, 0.3%, 0.4%, 0.5%, 0.6%, 0.7%, 0.8%, 0.9%, to 1.0%, 1.5%, 2.0%, 2.5%, 3.0%, 3.5%, 4.5%, or even 5.0% of $CH_4$. One specific example of a $H_2$-rich stream that may be produced from the process of this disclosure has the following molar composition: 0.25% of $CO_2$; 1.75% of CO; 93.87% of $H_2$; 0.23% of $N_2$; 3.63% of $CH_4$; and 0.29% of $H_2O$.

Where an even higher purity $H_2$ stream is desired, a portion of the $H_2$-rich stream can be further purified by using processes and technologies known to one skilled in the art, e.g., pressure-swing-separation.

Preferably, however, the $H_2$-rich stream, notwithstanding the optional low concentrations of CO, $CO_2$, and $CH_4$, is used as a fuel gas stream without further purification to provide heating in step (VIII) of the process in, e.g., residential, office, and/or industrial applications, preferably industrial applications. Due to the considerably reduced combined concentrations of CO, $CO_2$, and $CH_4$ therein compared to conventional fuel gases such as natural gas, the flue gas stream produced from combusting the $H_2$-rich stream can comprise $CO_2$ at a considerably reduced concentration, resulting in appreciably lower $CO_2$ emission to the atmosphere. Thus, the flue gas stream can comprise $CO_2$ at a molar concentration from, e.g., 0.01%, 0.05%, to 0.1%, 0.2%, 0.3%, 0.4%, 0.5%, 0.6%, 0.7%, 0.8%, 0.9%, to 1%, 2%, 3%, 4%, 5%, 6%, 7%, 8%, 9%, 10%, to 11%, 12%, 13%, 14%, 15%, 16%, 17%, 18%, 19%, or 20%, preferably ≤10%, preferably ≤5%, preferably ≤3%, based on the total moles of $CO_2$ and $H_2O$ in the flue gas stream. The combustion may be in the presence of, e.g., air, $O_2$-enhanced air, high-purity $O_2$, and the like, depending on the specific application.

For use as a fuel gas stream, the $H_2$-rich stream may preferably has an absolute pressure of ≤1,135 kPa (150 psig), preferably ≤790 kPa (100 psig). To achieve such low pressure of the $H_2$-rich stream, it is feasible to design a syngas producing unit upstream comprising an SMR and/or an ATR operating under syngas producing conditions including a relatively low pressure, e.g., an absolute pressure of ≤2,169 kPa (300 psig), preferably ≤1,825 kPa (250 psig). As mentioned above, a lower pressure in the reforming reactor results in a higher $CH_4$ conversion in the reforming reactor, and hence a low residual $CH_4$ concentration in the $H_2$-rich stream.

Preferably, the $H_2$-rich stream is supplied to at least one, preferably a majority, preferably all, of the combustion devices used in the process/system for producing the $H_2$-rich stream. Thus, where the syngas producing unit comprises a pre-reformer including a furnace heated by one or more burners combusting a fuel gas, preferably a portion of the $H_2$-rich stream is supplied as at least a portion, preferably a majority, preferably the entirety, of the fuel gas to such burners. Where the syngas producing unit includes an SMR comprising one or more SMR burners combusting a SMR fuel, it is highly desirable to supply a portion of the $H_2$-rich stream as at least a portion, preferably a majority, preferably the entirety, of the SMR fuel. Where the $H_2$-rich stream production process/system uses an additional boiler or auxiliary furnace combusting a fuel gas, it is desirable to supply a portion of the $H_2$-rich stream as at least a portion, preferably a majority, preferably the entirety, of the fuel gas. By combusting the $H_2$-rich stream and capturing the $CO_2$ stream, the $H_2$-rich stream production process/system of this disclosure can reach an appreciably reduced level of $CO_2$ emission to the atmosphere than conventional $H_2$ production processes combusting natural gas.

Compared to existing syngas and/or $H_2$-rich fuel gas producing processes, especially those combusting a hydrocarbon-containing fuel, the $H_2$-rich fuel gas production process of this disclosure has at least one of the following advantages: (i) lower capital investment and production cost due to, e.g., an absence of a PSA unit, a small-size $CO_2$ recovery unit, and operating the syngas producing unit, the first shift reactor, and the second shift gas reactor under relatively low pressure; and (ii) considerably lower $CO_2$ emission if the $CO_2$ stream is captured, stored, sequestered, and/or utilized.

Integration of the $H_2$-rich Fuel Gas Production Plant with an Olefins Production Plant A modern olefins production plant typically operates by feeding a hydrocarbon feed (e.g., ethane, propane, butanes, naphtha, crude oil, and mixtures and combinations thereof) and steam into a steam cracker, heating the hydrocarbon feed/steam mixture to an elevated cracking temperature for a desirable residence time, thereby cracking the hydrocarbon feed to produce a steam cracker effluent comprising $H_2$, $CH_4$, ethane, propane, butanes, C2-C4 olefins, C4 dienes, and C5+ hydrocarbons exiting the pyrolysis reactor. The heating can include a preheating step in the convection section of the steam cracker, followed by transfer to the radiant section, where additional heating to the elevated cracking temperature and cracking occur. The thermal energy need for the preheating in the convection section and the heating in the radiant section is typically provided by a plurality of steam cracker burners combusting a steam cracker fuel gas. The high-temperature steam cracker effluent is immediately cooled down by quenching and/or indirect heat exchange, and separated to produce, among others, a process gas stream comprising C1-C4 hydrocarbons. The process gas stream is then typically compressed and supplied to a product recovery section including a chill train and multiple distillation columns such as a demethanizer, a deethanizer, a depropanizer, a C2 splitter, a C3 splitter, to name a few, from which one of more of the following may be produced: (i) a steam-cracker $H_2$ stream, which may preferably comprise $H_2$ at a molar concentration of from, e.g., 80%, 81%, 82%, 83%, 84%, 85%, to 86%, 87%, 88%, 89%, 90%, to 91%, 92%, 93%, 94%, 95%, to 96%, 97%, or even 98%, based on the total moles of molecules in the steam-cracker $H_2$ stream; (ii) a $CH_4$-rich stream (sometimes referred to as a "tailgas stream") comprising $CH_4$ at a molar concentration from, e.g., 50%, 55%, 60%, 65%, 70%, to 75%, 80%, 85%, 90%, to 91%, 92%, 93%, 94%, 95%, 96%, 97%, or even 98%, based on the total moles of molecules in the $CH_4$-rich stream; (ii) an ethane stream; (iii) an ethylene product stream; (iv) a propane stream; and (v) a propylene product stream. Many configurations of the recovery sections are possible. The steam-cracker $H_2$ stream may comprise, on a molar basis, e.g., from 0.1%, 0.2%, 0.3%, 0.4%, 0.5%, 0.6%, 0.7%, 0.8%, 0.9%, to 1.0%, 1.5%, 2.0%, 2.5%, 3.0%, 3.5%, 4.5%, 5.0%, to 6.0%, 8.0%, 10%, 12%, 14%, 15%, to 16%, 17%, 18%, 19%, or even 20% of $CH_4$. Preferably the steam-cracker $H_2$ stream is substantially free of $CO_2$ and CO, e.g., comprising $CO_2$ and CO at a combined concentration from 0 to no greater than 1% by mole, based on the total moles of molecules in the steam-cracker $H_2$ stream. The $CH_4$-rich stream may comprise at least one and preferably all of, on a molar basis: (i) e.g., from 1%, 5%, 10%, 15%, to 20%, 25%, 30%, to 35%, or even 40%, 45% $H_2$; (ii) e.g., from 0.1%, 0.5%, 1%, to 2%, 3%, 4%, 5%, to 6%, 7%, 8%, 9%, or 10% ethane; and (iii) e.g., from 0.01%, 0.05%, 0.1%, to 0.2%, 0.5%, 1%, to 2%, 3%, 4%, or 5% CO, based on the total moles of molecules in the $CH_4$-rich stream.

The $H_2$-rich fuel gas production processes of this disclosure can be advantageously integrated with an olefins production plant to achieve an enhanced level of energy efficiency and a reduced level of $CO_2$ emissions to the atmosphere, regardless of the specific configuration of the recovery section in the plant.

In certain preferred embodiments, a portion of the $H_2$-rich stream may be combined with a portion of the steam-cracker $H_2$ stream to form a joint $H_2$-rich stream, which can be used as a fuel gas for residential, office, and/or industrial heating applications, including the heat applications described above for the $H_2$-rich stream.

In one particularly desirable embodiment, a portion of the $H_2$-rich stream, the steam-cracker $H_2$ stream, or the joint $H_2$-rich stream can be supplied to one of more of the steam cracker burners as at least a portion, preferably a majority, preferably the entirety, of the steam cracker fuel gas. A steam cracker can consume large quantity of the steam cracker fuel gas, which hitherto tends to comprise substantial quantity of hydrocarbons such as $CH_4$. By substituting a portion, preferably majority, preferably the entirety, of the steam cracker fuel gas with the $H_2$-rich stream, the steam-cracker $H_2$ stream, and/or the joint $H_2$-rich stream, each containing low concentrations of carbon-containing species, considerable reduction of $CO_2$ emission from the steam cracker flue gas can be achieved. In certain embodiments, the steam cracker may preferably be equipped with a combustion air pre-heater to reduce the fuel consumption requirements of the steam cracker. The combustion air pre-heater can preferably provide heating by electrical heating and/or exchanging heat with a warmer stream such as: the flue-gas of the same or different furnace; a steam stream (preferably a low-pressure steam stream), a hot water stream, and/or a hot oil stream.

An olefins production plant may include one or more boilers and/or auxiliary furnaces combusting a fuel gas in addition to the steam cracker. In such case, it is highly advantageous to supply a portion of the $H_2$-rich stream, the steam-cracker $H_2$ stream, and/or the joint $H_2$-rich stream to such boilers and/or auxiliary furnaces as a portion, preferably a majority, preferably the entirety, of the fuel gas needed. Doing so can further reduce $CO_2$ emission to the atmosphere from the olefins production plant.

An olefins production plant may comprise a combined-cycle power plant comprising one or more duct burners combusting a duct burner fuel to generate thermal energy. In such case, it is highly advantageous to supply a portion of the $H_2$-rich stream, the steam-cracker $H_2$ stream, and/or the joint $H_2$-rich stream to the duct burners as a portion, preferably a majority, preferably the entirety, of the duct burner fuel needed.

In certain embodiments, the $H_2$-stream and/or the steam-cracker $H_2$ stream can supply from, e.g., 60%, 65%, 70%, to 75%, 80%, 85%, to 90%, 95%, 98%, 99%, or even 100%, of the total fuel gas required, on a Btu basis, in the olefins production plant.

In one particularly advantageous embodiment, the $CH_4$-rich stream produced from the olefins production plant may be fed into the syngas producing unit as at least a portion of the hydrocarbon feed, along with, e.g., a natural gas stream. Since the $CH_4$-rich stream from the olefins production plant can be substantially free of sulfur, it can be advantageously fed into the syngas producing unit after the sulfur-removal unit, if any. If the $CH_4$-rich comprises C2+ hydrocarbons (e.g., ethane) at a low molar concentration, e.g., ≤3%, ≤2%, <1%, <0.5%, <0.1%, e.g., from 0.01%, 0.02%, 0.04%, 0.05%, to 0.06%, 0.08%, 0.1%, to 0.2%, 0.4%, 0.5%, to 0.6%, 0.8%, 1%, 2%, or even 3%, based on the total moles of hydrocarbons in the $CH_4$-rich stream, then the $CH_4$-rich stream can be supplied to the reforming reactor at a location downstream of the pre-reformer, if any, because of the reduced need to convert the C2+ hydrocarbons in the pre-reformer. The $CH_4$-rich stream may comprise $H_2$ at various quantities, as indicated above. However, it is not necessary to remove the $H_2$ from the $CH_4$-rich stream before it is fed to the SMR. Excess hydrogen in the $CH_4$-rich stream can consume hydraulic capacity in the SMR and hence is undesirable. But a small amount of hydrogen (preferably ≤10 mol %, preferably ≤5 mol %, based on the total moles of molecules in the $CH_4$-rich stream) is acceptable, and may actually serve to minimize the potential for coke or foulant generation in the SMR.

In certain embodiments, the $CH_4$-rich stream may have a pressure higher than the pressure of the hydrocarbon feed required for feeding into the syngas producing unit. In such case, it is highly advantageous to expand the $CH_4$-rich stream in a turbo-expander and/or a Joule-Thompson valve to produce a cooled $CH_4$-rich stream having a pressure in the vicinity of the pressure of the hydrocarbon feed. The cooled $CH_4$-rich stream may be heated by using, e.g., any stream in the olefins production plant or the $H_2$-rich production unit having a temperature higher than the cooled $CH_4$-rich stream, and then supplied to the syngas producing unit.

In certain embodiments, the $CH_4$-rich stream may have a pressure lower than the pressure of the hydrocarbon feed required for feeding into the syngas producing unit. In such case, it is desirable to compress the $CH_4$-rich stream to a pressure in the vicinity of the pressure of the hydrocarbon feed before feeding it to the syngas producing unit.

In the following TABLE I, the $CO_2$ footprint of a steam cracker combusting the following fuel gases emitting flue gases produced from the combustion are compared: (i) only a typical natural gas ("Natural Gas"); (ii) only a tailgas produced from a steam cracker receiving a typical naphtha steam-cracking feed ("Tailgas"); (iii) a CO-rich fuel gas produced from a comparison process including a syngas producing unit followed by a single stage of high-temperature shift reactor, and then followed by $H_2O$ abatement and $CO_2$ recovery ("CO-Rich Fuel"); and (iv) a $H_2$-rich stream made by the process of this disclosure ("$H_2$-Rich Fuel"). In all cases the following is assumed: 2.0 wet vol % excess $O_2$, 60° F. (16° C.) air & fuel gas.

As can be seen from TABLE I, compared to all other three fuel gases, the $H_2$-rich stream made by the process of this disclosure has a considerably smaller $CO_2$ footprint from the emission of the flue gas produced by the combustion. Even though the $H_2$-Rich Fuel only comprises $H_2$ at a lightly higher concentration and CO at a slightly lower concentration than the comparative CO-Rich Fuel, the $H_2$-Rich Fuel demonstrated a markedly lower $CO_2$ footprint (40% lower). This shows a significant advantage of the process of this disclosure utilizing at least two stages of shift reactors compared to using a single stage of high-temperature shift reactor only. While it is possible to purify the CO-Rich Fuel further to produce a fuel gas having a higher $H_2$ concentration and a lower CO concentration comparable to the H$_2$-Rich Fuel by using additional equipment such as a PSA unit, the installation and operation of a PSA unit add much more investment and operation costs and reduce the energy efficiency of the process than the addition of the second shift reactor. Therefore, the process of this disclosure achieves the production of a H$_2$-rich fuel gas with low CO$_2$ footprint with a reduced cost and enhanced energy efficiency.

TABLE I

| Fuel Gas | | Natural Gas | Tailgas | CO-Rich Fuel | H$_2$-Rich Fuel |
|---|---|---|---|---|---|
| Composition (mol %) | Hydrogen | 0.00 | 26.26 | 90.08 | 93.85 |
| | Methane | 94.11 | 73.33 | 3.63 | 3.63 |
| | Ethane | 4.76 | 0.23 | 0.00 | 0.00 |
| | Propane | 0.64 | 0.03 | 0.00 | 0.00 |
| | Butane | 0.30 | 0.02 | 0.00 | 0.00 |
| | Ethylene | 0.00 | 0.05 | 0.00 | 0.00 |
| | Propylene | 0.00 | 0.00 | 0.00 | 0.00 |
| | Butene | 0.00 | 0.00 | 0.00 | 0.00 |
| | Carbon Monoxide | 0.00 | 0.08 | 5.52 | 1.75 |
| | Nitrogen | 0.19 | 0.00 | 0.23 | 0.23 |
| | Carbon Dioxide | 0.00 | 0.00 | 0.25 | 0.25 |
| | Water Vapor | 0.00 | 0.00 | 0.29 | 0.29 |
| | Total | 100.00 | 100.00 | 100.00 | 100.00 |
| LHV (Btu/lb) | | 21295.5 | 22740.6 | 27059.5 | 35175.5 |
| Lb fuel/MBtu | | 46.96 | 43.97 | 36.96 | 28.43 |
| Lb flue-gas/Lb fuel | | 20.16 | 21.17 | 21.70 | 28.06 |
| Lb flue-gas/MBtu | | 946.5 | 930.8 | 801.9 | 797.7 |
| Flue-gas wt % CO$_2$ | | 13.68 | 12.41 | 4.57 | 2.77 |
| Flue-gas vol % CO$_2$ | | 8.60 | 7.72 | 2.66 | 1.59 |
| CO$_2$ Footprint | Lb/MBtu | 129.49 | 115.51 | 36.65 | 22.10 |
| | Lb/MBtu as % of Natural Gas Firing | 100 | 89 | 28 | 17 |
| | Lb/MBtu as % of Tailgas firing | 112 | 100 | 32 | 19 |
| | Lb/MBtu as % of CO-Rich Fuel Firing | 353 | 315 | 100 | 60 |

This disclosure is further illustrated by the exemplary but non-limiting embodiments shown in the drawings, which are described below. This disclosure is further illustrated by the exemplary but non-limiting embodiments shown in the drawings, which are described below. In the drawings, the same reference numeral may have similar meanings. In the drawings illustrating an inventive process/system, where multiple initially separate streams are shown to form a joint stream supplied to a next step or device, it should be understood to further include, where appropriate, an alternative where at least one of such multiple separate streams is supplied to the next step or device separately. Where multiple initially separate streams having similar compositions and/or use applications (steam streams generated from differing devices) are shown to form a joint stream supplied to multiple next steps or devices, it should be understood to include, where appropriate, alternatives where at least one of the separate streams and the joint stream is supplied to at least one of the multiple next steps or devices. Thus, where a steam stream X and a steam stream Y, initially separate and generated from differing devices but with similar applications, are shown to form a joint stream Z supplied to two separate turbines A and B, it should be understood to include alternatives where at least one of X, Y, and Z is supplied to at least one of A and B, including but not limited to the following: (i) only stream Z is supplied to A and B; (ii) both of X and Y are supplied, separately, to at least one of A and B; (iii) both of X and Z are supplied, separately, to at least one of A and B; (iv) both of Y and Z are supplied, separately, to at least one of A and B; and (v) only one of X and Y is supplied to at least one of A and B. The drawings are only for the purpose of illustrating certain embodiments of this disclosure, and one skilled in the art appreciates that alternatives thereof may fall within the scope of this disclosure.

FIG. 1

FIG. 1 schematically illustrates processes/systems 101 including an SMR for producing a H$_2$-rich fuel stream according to certain preferred embodiments of this disclosure. As shown, a hydrocarbon feed stream 103 (e.g., a natural gas stream comprising primarily CH$_4$), which may contain CH$_4$, C2+ hydrocarbons at various concentrations, and sulfur-containing compounds at various concentrations, is first fed into an optional sulfur removal unit 105 to produce a sulfur-abated stream 107, to prevent poisoning catalysts used in the downstream process steps such as the catalyst used in the SMR unit described below. Upon optional preheating via, e.g., a heat exchanger or a furnace (not shown), stream 107 is combined with an HPS stream 179 to form a hydrocarbon/steam mixture stream 109. Upon optional preheating via, e.g., a heat exchanger or a furnace (not shown), stream 109 can be then fed into a pre-reformer 111 which can be an adiabatic reactor containing a pre-reforming catalyst therein. On contacting the pre-reforming catalyst, the heavier C2+ hydrocarbons are preferentially converted into methane (thus preventing the formation of coke in the downstream primary reforming reactor) to produce a pre-reforming effluent 113 comprising methane and steam. Stream 113 is then fed into a tube 120a in the upper section 114, sometimes called convection section, of an SMR 115, where it is heated. SMR 115 comprises a lower section 116, sometimes called radiant section, housing one or more tube 120b which is in fluid communication with tube 120a receiving the stream 113 heated in tube 120a. As shown in FIG. 1, tube 120a may exit the convection section to the exterior of the SMR furnace, and then re-enters at the entrance to tube(s) 120b, via, e.g., a manifold (not shown). SMR 115 comprises one or more burners 118 in the radiant section 116, where a SMR fuel combusts to supply energy to the radiant section 116 and then the convection section 114 of SMR 115. For the convenience of illustration, tubes 120a and 120b in the SMR are shown as comprising multiple straight segments. In practice, certain portions of tubes 120a and 120b, particularly tube 120a, may be curved, or even form serpentine windings.

A reforming catalyst is loaded in tube(s) 120b in the radiant section 116. Due to the proximity to the burner(s) 118, the hydrocarbon feed and steam, and the reforming catalyst in tube(s) 120b are heated/maintained at an elevated temperature. The forward reaction of the following preferentially occurs under syngas producing conditions:

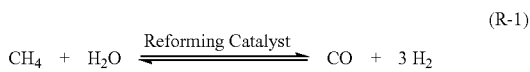

(R-1)

In addition, various amounts of CO$_2$ may be produced in tube(s) 120b. Thus, a reformed stream 121 comprising CO, H$_2$, residual CH$_4$, residual H$_2$O and optionally various amount of CO$_2$ exits the outlet of tube(s) 120b from the SMR at a temperature of, e.g., from 750° C. to 900° C. and an absolute pressure of, e.g., from 700 kPa to 3,500 kPa. Stream 121 is then cooled at a waste heat recovery unit ("WHRU") including a waste heat boiler ("WHB") 123 and a steam drum 171 to produce a cooled reformed stream 125 and to generate an HPS stream 167. As shown, a water stream 163 flows from steam drum 171 to WHB 123, and a steam-water mixture stream 165 flows from WHB 123 to steam drum 171.

Stream 167, preferentially a saturated steam stream, can be then heated in the convection section 114 of SMR 115 to produce a super-heated, high-pressure steam ("SPHP") steam stream 169, which can be fed into a steam header and supplied to any suitable equipment or process step. For example, as shown and described above, a split stream 179 of stream 169 can be combined with the sulfur-abated hydrocarbon feed stream 107 to form a combined stream 109, which is then fed into the pre-reformer 111. For another example, a split stream 177 of stream 169 can be fed into a steam turbine 173, where it is expanded to produce an exhaust steam stream 183 and shaft power. The shaft power can be transferred, via shaft 181, to any suitable equipment 175 to produce useful mechanical work. One example of equipment 175 is an electricity generator, which converts the mechanical work into electrical energy transmissible to any suitable local or distant electrical equipment. Exhaust steam stream 183 can have various residual pressure and temperature suitable for, e.g., driving additional steam turbines, heating other equipment and/or streams, and the like.

As shown in FIG. 1, the cooled reformed stream 125, comprising CO, H$_2$, H$_2$O, and optionally CO$_2$, is then fed into a first shift reactor 127. The first shift reactor can be operated under a first set of shifting conditions comprising the presence of a first shift catalyst loaded therein. Due to the relatively high temperature in the first set of shifting conditions, the first shift reactor 127 is sometimes called a high-temperature shift reactor. On contacting the first shift catalyst under the first set of shifting conditions, the forward reaction of the following preferentially occurs:

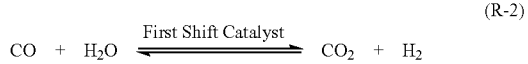

(R-2)

Thus, a first shifted stream 129 comprising CO at a lower concentration than stream 125 and CO$_2$ at a higher concentration than stream 125 exits the first shift reactor 127. Because the forward reaction above is exothermic, stream 129 has a higher temperature than stream 125 assuming the first shift reactor 127 is an adiabatic reactor.

The first shifted stream 129 can then be further cooled down at heat exchanger 131 by any suitable stream having a temperature lower than stream 129. As shown in FIG. 1, in a preferred embodiment, a boiler feed water stream 134, supplied from a boiler feed water treatment unit 133, is used to cool down stream 129. The thus heated boiler feed water stream 135 exiting the heat exchanger 131 can be supplied to steam drum 171 and at least partly supplied to the WHB 123, to produce high-pressure steam stream 167 as described earlier, or to any other suitable steam generator. Alternatively or additionally (not shown), the hydrocarbon feed stream 103, or a portion thereof, may be heated by stream 129 at heat exchanger 131 or another heat exchanger upstream or downstream of heat exchanger 131.

The cooled first shifted stream 136 exiting heat exchanger 131, comprising CO, H$_2$, H$_2$O, and CO$_2$, is then fed into a second shift reactor 137. The second shift reactor can be operated under a second set of shifting conditions comprising the presence of a second shift catalyst loaded therein and a temperature lower than in the first shift reactor 127. Due to the lower temperature, the second shift reactor 137 is sometimes called a low-temperature shift reactor. On contacting the second shift catalyst under the second set of shifting conditions, the forward reaction of the following preferentially occurs:

(R-3)

Thus, a second shifted stream 139 comprising CO at a lower concentration than stream 136 and CO$_2$ at a higher concentration than stream 136 exits the second shift reactor 137. Because the forward reaction above is exothermic, stream 139 has a higher temperature than stream 136 assuming the second shift reactor 137 is an adiabatic reactor.

The second shifted stream 139 can then be further cooled down at heat exchanger 141 by any suitable stream having a temperature lower than stream 139. In a preferred embodiment, a boiler feed water stream (not shown) supplied from a boiler feed water treatment unit (e.g., unit 133) can be advantageously used to cool down stream 139. The thus heated boiler feed water stream exiting the heat exchanger 141 can be supplied (not shown) to steam drum 171 and at least partly supplied to the WHB 123, to produce high-pressure steam stream 167 as described earlier, or to any other suitable steam generator. Alternatively or additionally (not shown), the hydrocarbon feed stream 103, or a portion thereof, may be heated by stream 139 at heat exchanger 141 or another heat exchanger upstream or downstream of heat exchanger 141.

The cooled stream 143 exiting heat exchanger 141 can be further cooled at heat exchanger 145 by any suitable cooling medium having a lower temperature than stream 143, e.g., a cooling water stream, ambient air (using an air-fin cooler, e.g.), and the like. Preferably, a portion of the residual steam in stream 143 is condensed to liquid water in stream 147, which can be fed into a separator 149 to obtain a condensate stream 151 and a vapor stream 153. The steam-abated stream 153, a crude gas mixture, comprises primarily H$_2$ and CO$_2$, and optionally minor amount of residual CH$_4$ and CO.

Stream 153 can then be supplied into a CO$_2$ recovery unit 155 to produce a CO$_2$ stream 157 and an H$_2$-rich stream 159. Any suitable CO$_2$ recovery unit known in the art may be used. A preferred CO$_2$ recovery unit is an amine absorption and regeneration unit, where the crude gas mixture stream 153 contacts a counter-current stream of amine which absorbs the CO$_2$, which is subsequently released from the amine upon heating ("regeneration"). The CO$_2$ stream 157 can be supplied to a CO$_2$ pipeline and conducted away. The CO$_2$ stream 157 can be compressed, liquefied, stored, sequestered, or utilized in manners known to one skilled in the art.

The H$_2$-rich stream 159 can advantageously comprise H$_2$ at a molar concentration from, e.g., 80%, 81%, 82%, 83%, 84%, 85%, to 86%, 87%, 88%, 89%, 90%, to 91%, 92%, 93%, 94%, 95%, to 96%, 97%, 98%, 99%, based on the total moles of molecules in stream 159. In addition to H$_2$, stream 159 may comprise: (i) CH$_4$ at a molar concentration thereof based on the total moles of molecules in stream 159, from, e.g., 0.1%, 0.3%, 0.5%, 0.8%, to 1%, 2%, 3%, 4%, or 5%; (ii) CO at a molar concentration thereof based on the total moles of molecules in stream 159, from, e.g., 0.1%, 0.3%, 0.5%, 0.8%, to 1%, 2%, or 3%; and (iii) CO$_2$ at a molar concentration thereof based on the total moles of molecules in stream 159, from, e.g., 0.1%, 0.2%, 0.3%, 0.4%, 0.5%, to 0.6%, 0.7%, 0.8%, 0.9%, or 1%. Stream 159 can be advantageously used as a fuel gas for residential, office, and/or industrial heating. Due to the high concentration of $H_2$ and low concentration of carbon-containing molecules therein, the combustion of stream 159 in the presence of an oxidant such as air, oxygen, and the like, can produce a flue gas stream comprising $CO_2$ at a low concentration. In certain embodiments, the flue gas stream can comprises $CO_2$ at a molar concentration based on the total moles of $H_2O$ and $CO_2$ in the flue gas stream of no greater than 20% (e.g., from 0.1%, 0.2%, 0.4%, 0.5%, to 0.6%, 0.8%, 1%, to 2%, 4%, 5%, to 6%, 8%, 10%, to 12%, 14%, 15%, to 16%, 18 mol %, or 20%). The flue gas stream can be advantageously exhausted into the atmosphere without the need to separate and capture $CO_2$ therefrom.

In a preferred embodiment, as shown in FIG. 1, a split stream 117 of stream 159 can be supplied to the SMR 115, where it is combusted in burner(s) 118 to supply thermal energy to the SMR 115 heating the lower radiant section 116 and tube(s) 120b therein and the convection section 114 and tube 120a therein. The flue gas stream 119 exiting the SMR 115 comprises $CO_2$ at a low concentration, and therefore can be exhausted into the atmosphere with considerably reduced $CO_2$ emission without the need to separate and capture $CO_2$ therefrom.

FIG. 2

Figure 2:
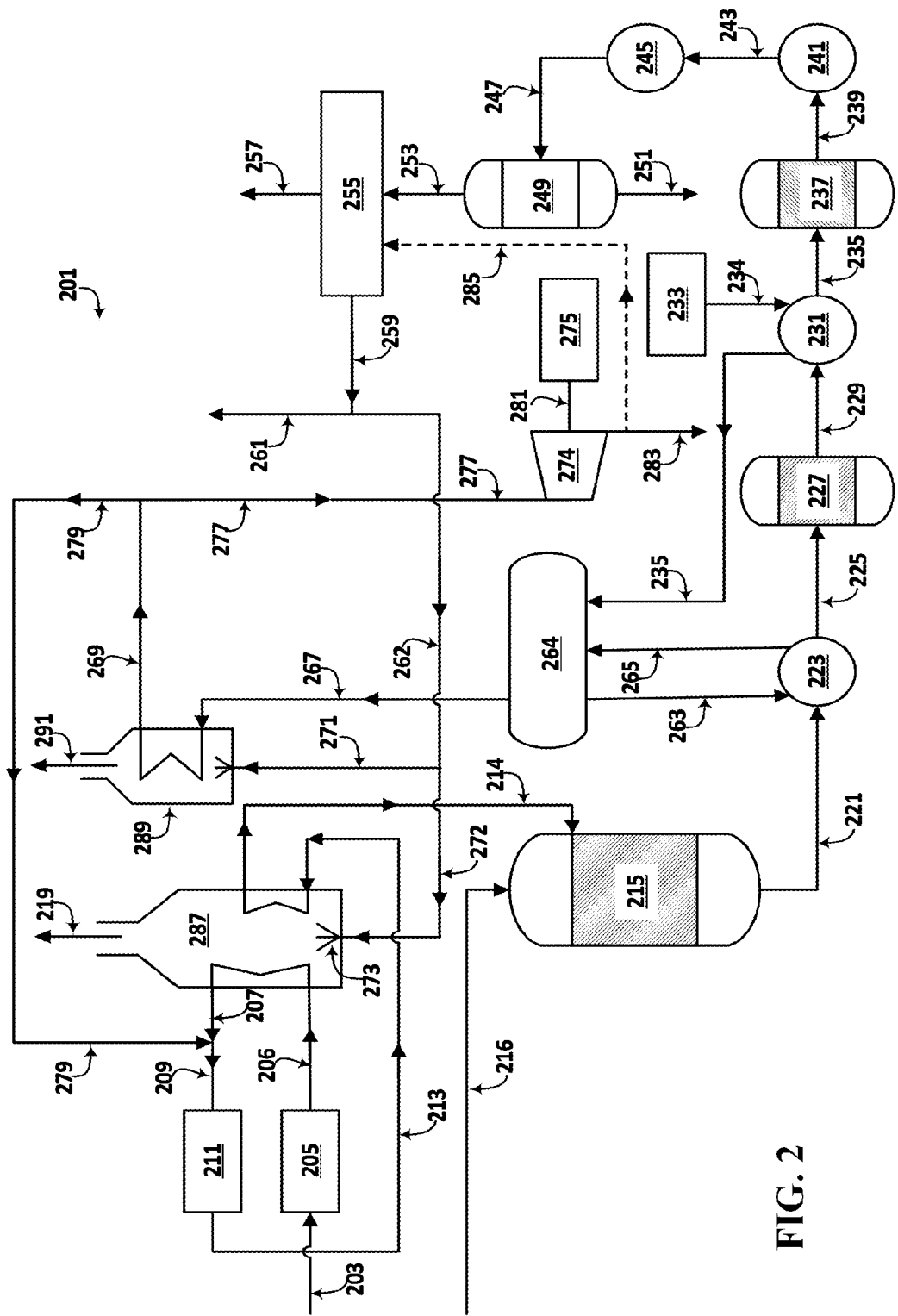
FIG. 2 schematically illustrates certain processes and systems for producing a $H_2$-rich stream including an ATR according to certain embodiments of this disclosure.

FIG. 2 schematically illustrates processes/systems 201 including an ATR for producing a $H_2$-rich fuel stream according to certain preferred embodiments of this disclosure. As shown, a hydrocarbon feed stream 203 (e.g., a natural gas stream comprising primarily $CH_4$), which may contain $CH_4$, C2+ hydrocarbons at various concentrations, and sulfur-containing compounds at various concentrations, is first fed into an optional sulfur removal unit 205 to produce a sulfur-abated stream 206, to prevent poisoning catalysts used in the downstream process steps such as the catalyst used in the pre-reformer and the ATR unit described below. Upon optional preheating via, e.g., a heat exchanger (not shown) or a furnace 287 a heated stream 207 is produced. Stream 207 is then combined with an HPS stream 279 to form a hydrocarbon/steam mixture stream 209. Upon optional preheating via, e.g., a heat exchanger or a furnace (not shown), stream 209 can be then fed into a pre-reformer 211 which can be an adiabatic reactor containing a pre-reforming catalyst therein. On contacting the pre-reforming catalyst, the heavier C2+ hydrocarbons are preferentially converted into methane (thus preventing the formation of coke in the downstream primary reforming reactor) to produce a pre-reforming effluent 213 comprising methane and steam. Upon optional heating in furnace 287, stream 213 becomes a heated stream 214, which is then fed into an ATR 215, an $O_2$ stream 216, which may be produced by air separation, is also fed into ATR 215.

A reforming catalyst is loaded in ATR 215. On contacting the reforming catalyst, the forward reaction of the following preferentially occurs under syngas producing conditions:

(R-1)

In addition, various amounts of $CO_2$ may be produced in the ATR. Thus, a reformed stream 221 comprising CO, $H_2$, residual $H_2O$, optionally residual $CH_4$ at various concentrations, and optionally various amount of $CO_2$ exits ATR 115 at a temperature of e.g., from 800° C. to 1200° C. and an absolute pressure from 700 kPa to 5,000 kPa. Stream 221 is then cooled at a waste heat recovery unit ("WHRU") including a waste heat boiler ("WHB") 223 and a steam drum 264 to produce a cooled reformed stream 225 and to generate an HPS stream 267. As shown, a water stream 263 flows from steam drum 264 to WHB 223, and a steam-water stream 265 flows from WHB 223 to steam drum 264.

Stream 267, preferentially a saturated steam stream, can be then heated in an auxiliary furnace 289 to produce a super-heated, high-pressure steam ("SH-HPS") stream 269, which can be fed into a steam header and supplied to any suitable equipment or process step. Furnace 289 may be the same furnace as furnace 287 or a separate furnace. For example, as shown and described above, a split stream 279 of stream 269 can be combined with the sulfur-abated hydrocarbon feed stream 207 to form a combined stream 209, which is then fed into the pre-reformer 211. For another example, a split stream 277 of stream 269 can be fed into a steam turbine 274, where it is expanded to produce an exhaust steam stream 283 and shaft power.

The shaft power can be transferred, via shaft 281, to any suitable equipment 275 to produce useful mechanical work. One example of equipment 275 is an electricity generator, which converts the mechanical work into electrical energy transmissible to any suitable local or distant electrical equipment. Exhaust steam stream 283 can have various residual pressure and temperature suitable for, e.g., driving additional steam turbines, heating other equipment and/or streams, and the like.

As shown in FIG. 2, the cooled reformed stream 225, comprising CO, $H_2$, $H_2O$, and optionally $CO_2$, is then fed into a first shift reactor 227. The first shift reactor can be operated under a first set of shifting conditions comprising the presence of a first shift catalyst loaded therein. Due to the relatively high temperature in the first set of shifting conditions, the first shift reactor 227 is sometimes called a high-temperature shift reactor. On contacting the first shift catalyst under the first set of shifting conditions, the forward reaction of the following preferentially occurs:

(R-2)

Thus, a first shifted stream 229 comprising CO at a lower concentration than stream 225 and $CO_2$ at a higher concentration than stream 225 exits the first shift reactor 227. Because the forward reaction above is exothermic, stream 229 has a higher temperature than stream 225 assuming the first shift reactor 227 is an adiabatic reactor.

The first shifted stream 229 can then be further cooled down at heat exchanger 231 by any suitable stream having a temperature lower than stream 229. As shown in FIG. 2, in a preferred embodiment, a boiler feed water stream 234, supplied from a boiler feed water treatment unit 233, can be used to cool down stream 229. The thus heated boiler feed water stream 235 exiting the heat exchanger 231 can be supplied to steam drum 264 and at least partly subsequently supplied to the WHB 223, to produce high-pressure steam stream 267 as described earlier, or to any other suitable steam generator. Alternatively or additionally (not shown), the hydrocarbon feed stream 203, or a portion thereof, may be heated by stream 229 at heat exchanger 231 or another heat exchanger upstream or downstream of heat exchanger 231.

The cooled first shifted stream 235 exiting heat exchanger 231, comprising CO, $H_2$, $H_2O$, and $CO_2$, is then fed into a second shift reactor 237. The second shift reactor can be operated under a second set of shifting conditions comprising the presence of a second shift catalyst loaded therein and a temperature lower than in the first shift reactor 227. Due to the lower temperature, the second shift reactor 237 is sometimes called a low-temperature shift reactor. On contacting the second shift catalyst under the second set of shifting conditions, the forward reaction of the following preferentially occurs:

(R-3)

Thus, a second shifted stream 239 comprising CO at a lower concentration than stream 235 and $CO_2$ at a higher concentration than stream 235 exits the second shift reactor 237. Because the forward reaction above is exothermic, stream 239 has a higher temperature than stream 236 assuming the second shift reactor 237 is an adiabatic reactor.

The second shifted stream 239 can then be further cooled down at heat exchanger 241 by any suitable stream having a temperature lower than stream 239. In a preferred embodiment, a boiler feed water stream (not shown) supplied from a boiler feed water treatment unit (e.g., unit 233) can be advantageously used to cool down stream 239. The thus heated boiler feed water stream exiting the heat exchanger 241 can be supplied (not shown) to steam drum 264 and at least partly supplied to the WHB 223, to produce high-pressure steam stream 267 as described earlier, or to any other suitable steam generator. Alternatively or additionally (not shown), the hydrocarbon feed stream 203, or a portion thereof, may be heated by stream 239 at heat exchanger 241 or another heat exchanger upstream or downstream of heat exchanger 241.

The cooled stream 243 exiting heat exchanger 241 can be further cooled at heat exchanger 245 by any suitable cooling medium having a lower temperature than stream 243, e.g., a cooling water stream, ambient air (using an air-fin cooler, e.g.), and the like. Preferably, a portion of the residual steam in stream 243 is condensed to liquid water in stream 247, which can be fed into a separator 249 to obtain a condensate stream 251 and a vapor stream 253. The steam-abated stream 253, a crude gas mixture stream, comprises primarily $H_2$ and $CO_2$, and optionally minor amount of residual $CH_4$ and CO.

Stream 253 can then be supplied into a $CO_2$ recovery unit 255 to produce a $CO_2$ stream 257 and an $H_2$-rich stream 259. Any suitable $CO_2$ recovery unit known in the art may be used. A preferred $CO_2$ recovery unit is an amine absorption and regeneration unit, where the crude gas mixture stream 253 contacts a counter-current stream of amine which absorbs the $CO_2$, which is subsequently released from the amine upon heating ("regeneration"). The $CO_2$ stream 257 can be supplied to a $CO_2$ pipeline and conducted away. The $CO_2$ stream 257 can be compressed, liquefied, stored, sequestered, or utilized in manners known to one skilled in the art.

The $H_2$-rich stream 259 can advantageously comprise $H_2$ at a molar concentration from, e.g., 80%, 81%, 82%, 83%, 84%, 85%, to 86%, 87%, 88%, 89%, 90%, to 91%, 92%, 93%, 94%, 95%, to 96%, 97%, 98%, 99%, based on the total moles of molecules in stream 259. In addition to $H_2$, stream 259 may comprise: (i) $CH_4$ at a molar concentration thereof based on the total moles of molecules in stream 259, from, e.g., 0.1%, 0.3%, 0.5%, 0.8%, to 1%, 2%, 3%, 4%, or 5%; (ii) CO at a molar concentration thereof based on the total moles of molecules in stream 259, from, e.g., 0.1%, 0.3%, 0.5%, 0.8%, to 1%, 2%, or 3%; and (iii) $CO_2$ at a molar concentration thereof based on the total moles of molecules in stream 259, from, e.g., 0.1%, 0.2%, 0.3%, 0.4%, 0.5%, to 0.6%, 0.7%, 0.8%, 0.9%, or 1%. Stream 259 can be advantageously used as a fuel gas for residential, office, and/or industrial heating. Due to the high concentration of $H_2$ and low concentration of carbon-containing molecules therein, the combustion of stream 259 in the presence of an oxidant such as air, oxygen, and the like, can produce a flue gas stream comprising $CO_2$ at a low concentration. In certain embodiments, the flue gas stream can comprises $CO_2$ at a molar concentration based on the total moles of $H_2O$ and $CO_2$ in the flue gas stream of no greater than 20% (e.g., from 0.1%, 0.2%, 0.4%, 0.5%, to 0.6%, 0.8%, 1%, to 2%, 4%, 5%, to 6%, 8%, 10%, to 12%, 14%, 15%, to 16%, 18 mol %, or 20%). The flue gas stream can be advantageously exhausted into the atmosphere without the need to separate and capture $CO_2$ therefrom.

In a preferred embodiment, as shown in FIG. 2, a split stream 272 of stream 262 (which is a split stream of stream 259) can be supplied to furnace 287, where it is combusted to preheat the de-sulfured hydrocarbon stream 206, and a split stream 271 of stream 262 can be supplied to furnace 289, where it is combusted to superheat steam stream 267. The flue gas streams 219 and 291 exiting furnaces 287 and 289 comprise $CO_2$ at a low concentration, and therefore can be exhausted into the atmosphere without the need to separate and capture $CO_2$ therefrom.

FIG. 3

Figure 3:
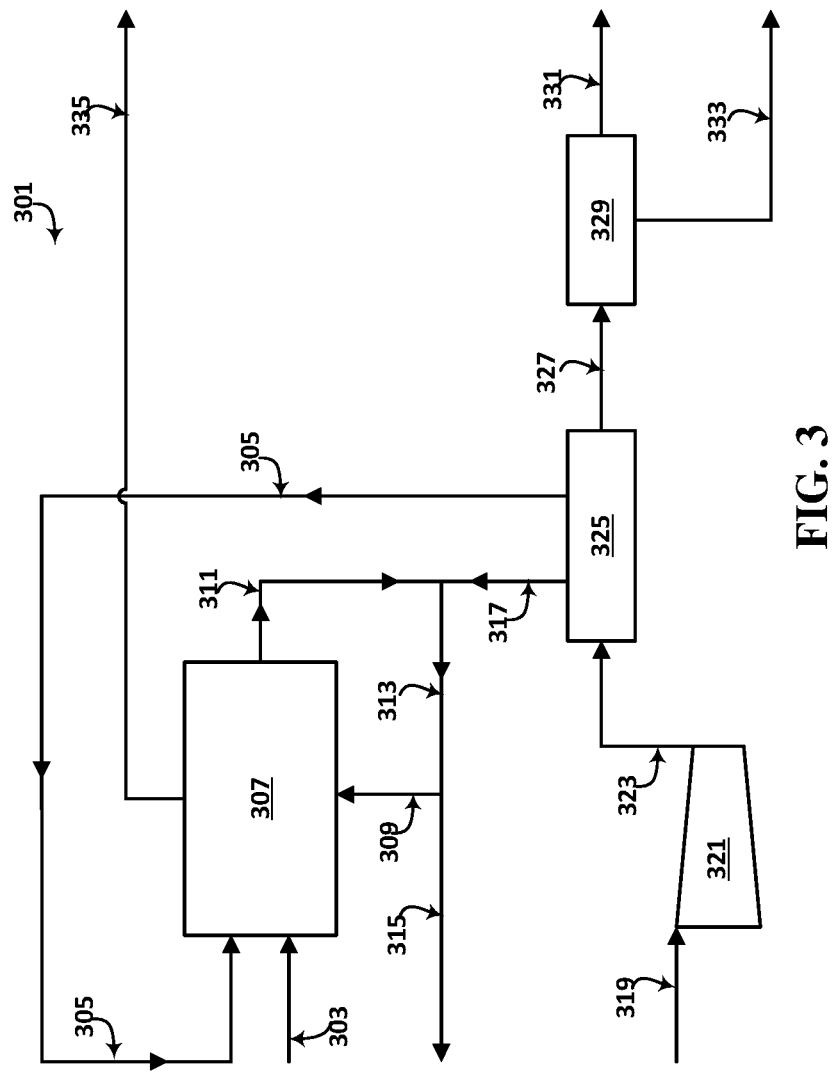
FIG. 3 schematically illustrates processes and systems integrating an olefins production plant with an $H_2$-rich fuel gas production unit according to certain preferred embodiments of this disclosure.

FIG. 3 is a block diagram schematically illustrating processes and systems integrating an olefins production plant with an $H_2$-rich fuel gas production unit as described above, according to certain preferred embodiments of this disclosure. The olefins production plant can include a pyrolysis reactor (e.g., a steam cracker) receiving a hydrocarbon feed and steam, preheating the hydrocarbon feed in a convection section, transferring the preheated feed and steam into a radiant section, subjecting the hydrocarbon feed and steam in the radiant section to suitable pyrolysis conditions including an elevated temperature and a short residence time, thereby producing a pyrolysis effluent comprising olefins such as ethylene, propylene, C4 olefins, C4 dienes, and methane, ethane, propane, and C5+ hydrocarbons. The pyrolysis effluent is typically immediately cooled down by quenching and/or indirect heat transfer, and subsequently separated in a primary fractionator and/or a quench tower to produce, among others, a process gas stream 319 comprising $H_2$, $CH_4$, ethane, propane, and the desirable C2-C4 olefins and dienes. The process gas stream 319 is typically compressed in one or more compressor(s) 321 to an elevated pressure, and then cooled down in a chill train and separated in a cryogenic product recovery system 325. The product recovery system 325 can include a demethanizer, a deethanizer, a depropanizer, and the like, arranged in various configurations. From the product recovery system 325, a steam-cracker $H_2$ stream 317, a $CH_4$-rich tailgas stream 305, and a C2 hydrocarbon stream 327, among others, can be produced. The C2 hydrocarbon stream 327 can be further separated in a C2 splitter tower 329 to produce an ethylene product stream 331 and an ethane stream 333, the latter of which can be advantageously recycled to the steam cracker and cracked to produce additional quantities of olefin products.

As show in FIG. 3, the $CH_4$-rich stream 305 and an optional supplemental hydrocarbon stream 303 (e.g., a natural gas stream) can be supplied along with steam (not shown)

into a $H_2$-rich fuel gas production unit 307 as hydrocarbon feeds. The $H_2$-rich fuel gas production unit 307 can include a reforming reactor such as an SMR or an ATR, a first shift reactor, a second shift reactor, a $CO_2$ recovery unit and ancillary equipment, such as those described above and illustrated in FIGS. 1 and 2. From unit 307, an $H_2$-rich fuel gas stream 311 and a $CO_2$ stream 335 can be produced. The $H_2$-rich fuel gas stream 311 can be advantageously combined with the steam-cracker $H_2$ stream 317 produced from the recovery system 325 of the olefins production plant to form a joint $H_2$-rich fuel gas stream 313. A portion of streams 311, 313, and/or 317, such as split stream 309 as shown in FIG. 3, may be fed into the $H_2$-rich fuel gas production unit 307 as industrial fuel needed by various equipment therein, e.g., a furnace heating any pre-reformer, an SMR, any additional furnaces, boilers, and the like. A portion of streams 311, 313, and/or 317, such as split stream 315 as shown in FIG. 1, may be supplied to the olefins product plant as industrial fuel needed by various equipment therein, e.g., a steam cracker furnace, any supplemental furnace, and boilers. The combustion of the $H_2$-rich fuel gas in the $H_2$-rich fuel gas production unit 307 and in the olefins production plant can result in appreciably reduced $CO_2$ emission into the atmosphere compared to combustion of hydrocarbons such as natural gas.

The $CO_2$ stream 335 can be compressed, liquefied, conducted away, stored, sequestered, or utilized for suitable applications such as underground hydrocarbon extraction. As a result, processes and systems integrating an olefins production plant with an $H_2$-rich fuel gas production unit as shown in FIG. 3 can achieve a desirably reduced overall $CO_2$ emission and a desirably improved overall energy efficiency compared to stand-alone processes.

Listing of Embodiments

This disclosure can additionally include one or more of the following non-limiting embodiments:

A1. A process comprising:

(I) supplying a hydrocarbon feed and a steam feed into a syngas producing unit comprising a reforming reactor under syngas producing conditions to produce a reformed stream exiting the reforming reactor, wherein the syngas producing conditions include the presence of a reforming catalyst, and the reformed stream comprises $H_2$, CO, and steam;

(II) cooling the reformed stream by using a waste heat recovery unit ("WHRU") to produce a cooled reformed stream and to generate a high-pressure steam ("HPS") stream;

(III) contacting the cooled reformed stream with a first shifting catalyst in a first shift reactor under a first set of shifting conditions to produce a first shifted stream exiting the first shift reactor, wherein the first shifted stream has a lower CO concentration and a higher $CO_2$ concentration than the cooled reformed stream;

(IV) cooling the first shifted stream to obtain a cooled first shifted stream;

(V) contacting the cooled first shifted stream with a second shifting catalyst in a second shift reactor under a second set of shifting conditions to produce a second shifted stream exiting the second shift reactor, wherein the second shifted stream has a lower CO concentration and a higher $CO_2$ concentration than the cooled first shifted stream;

(VI) abating steam present in the second shifted stream to produce a crude gas mixture stream comprising $CO_2$ and $H_2$;

(VII) recovering at least a portion of the $CO_2$ present in the crude gas mixture stream to produce a $CO_2$ stream and a $H_2$-rich stream, wherein the $H_2$-rich stream comprises $H_2$ at a concentration of at least 80 mol %, based on the total moles of molecules in the $H_2$-rich stream;

(VIII) combusting a portion of the $H_2$-rich stream in the presence of an oxidant to generate thermal energy and to produce a flue gas stream;

(IX) operating a steam cracker located in an olefins production plant under steam cracking conditions to convert a steam cracker feed into a steam cracker effluent comprising olefins;

(X) producing a $CH_4$-rich stream from the steam cracker effluent; and (XI) providing the $CH_4$-rich stream as at least a portion of the hydrocarbon feed in step (I).

A2. The process of A1, wherein the flue gas stream in step (VIII) comprises $CO_2$ at a concentration no greater than 20 mol % based on the total moles of $H_2O$ and $CO_2$ in the flue gas stream.

A3. The process of A2, wherein the flue gas stream in step (VIII) comprises $CO_2$ at a concentration no greater than 10 mol % (preferably no greater than 5 mol %, preferably no greater than 3 mol %), based on the total moles of $H_2O$ and $CO_2$ in the flue gas stream.

A4. The process of any of A1 to A3, wherein the $H_2$-rich stream comprises $H_2$ at a concentration of at least 85 mol % (preferably at least 90 mol %, preferably at least 95 mol %) based on the total moles of molecules in the $H_2$-rich stream.

A5. The process of A4, wherein the $H_2$-rich stream further comprises at least one and preferably all of: ≤5 mol % of $CH_4$; ≤3 mol % CO; and ≤1 mol % $CO_2$, based on the total moles of molecules in the $H_2$-rich stream.

A5.1. The process of any of A1 to A5, wherein the reformed stream has at least one of the following: a temperature of at least 750° C., and an absolute pressure from 700 kPa to 5000 kPa.

A6. The process of any of A1 to A5.1, wherein the cooled reformed stream produced in step (II) has a temperature from 285° C. to 400° C.

A7. The process of any of A1 to A6, wherein the HPS stream generated in step (II) has an absolute pressure from 4,000 to 14,000 kPa.

A8. The process of any of A1 to A7, wherein step (III) has at least one of the following features (a) and (b):

(a) the first set of shifting conditions comprise an absolute pressure from 700 to 5,000 kPa; and (b) the first shifted stream has at least one of the following: a temperature from 335 to 500° C.; and an absolute pressure from 700 kPa to 5,000 kPa.

A9. The process of any of A1 to A8, wherein step (IV) comprises cooling the first shifted stream, via a heat exchanger, by a cooling stream selected from: a stream comprising the hydrocarbon feed; a boiler feed water stream; and combinations thereof.

A10. The process of any of A1 to A9, wherein the cooled first shifted stream has at least one of the following: a temperature from 150 to 250° C., and an absolute pressure from 700 to 5,000 kPa.

A11. The process of any of A1 to A10, wherein in step (V), the second shifted stream has at least one of the following: a temperature from 150 to 300° C.; and an absolute pressure from 700 to 5000 kPa; and a CO concentration no greater than 5.0 mol %, based on the total moles of molecules in the second shifted stream.

A12. The process of any of A1 to A11, wherein step (VI) comprises:

(VIa) cooling the second shifted stream to condense a portion of steam in the second shifted stream to form liquid water and to obtain a cooled second shifted stream; and (VIb) separate the liquid water from the cooled second shifted stream to obtain the crude gas mixture stream.

A13. The process of A12, wherein step (VII) comprises at least one of the following:

(VIIa) separating at least a portion of the crude gas mixture by using an amine absorption and regeneration process;

(VIIb) separating at least a portion of the gas mixture by using a cryogenic $CO_2$ separation process;

(VIIc) separating at least a portion of the gas mixture by using a membrane separation process; and (VIId) separating at least a portion of the gas mixture by using a physical absorption and regeneration process.

A14. The process of any of A1 to A13, wherein the syngas producing unit comprises a steam-methane-reformer ("SMR") and/or an autothermal reformer ("ATR").

A15. The process of A14, wherein:

the syngas producing unit comprises a SMR;

the SMR comprises: one or more SMR burners where a SMR fuel combusts to supply thermal energy to the SMR; a radiant section heated by the thermal energy in which the hydrocarbon feed and steam react under the syngas producing conditions; a convection section heated by the thermal energy in which the hydrocarbon feed and steam are preheated before entering the radiant section; and in step (VII), a portion of the $H_2$-rich stream is supplied to the plurality of SMR burners as at least a portion of the SMR fuel.

A16. The process of claim A15, wherein in step (VII), a portion of the $H_2$-rich stream is supplied to the one or more SMR burners as the entirety of the SMR fuel.

A17. The process of A15 or A16, wherein the reformed stream has at least one of the following: a temperature from 750° C. to 900° C.; and an absolute pressure from 700 kPa to 3,500 kPa.

A18. The process of any of A15 to A17, further comprising:

(XII) heating the HPS stream generated in step (II) in the convection section of the SMR and/or an auxiliary furnace to obtain a super-heated HPS ("SH-HPS") stream having at least one of the following: a temperature from 350° C. to 550° C., and a pressure from 4,000 kPa to 14,000 kPa.

A19. The process of A14, wherein:

the syngas producing unit comprises an ATR;

an $O_2$ stream is fed into the ATR;

the ATR comprises a reaction vessel into which the hydrocarbon feed, the steam feed, and the $O_2$ stream are supplied;

the syngas producing conditions comprises the presence of an ATR catalyst in the reaction vessel; and the reformed stream has at least one of the following: a temperature from 800° C. to 1200° C.; and an absolute pressure from 2,000 kPa to 5,000 kPa.

A20. The process of A19, wherein the HPS stream generated in step (II) has an absolute pressure from 4,000 to 14,000 kPa.

A21. The process of A19 or A20, further comprising:

(XIIa) heating the HPS stream generated in step (II) in an auxiliary furnace to obtain a super-heated HPS ("SH-HPS") stream having at least one of the following: a temperature from 350° C. to 550° C., and a pressure from 4,000 kPa to 14,000 kPa.

A22. The process of A21, wherein the auxiliary furnace additionally preheats the hydrocarbon feed and/or the steam feed before the hydrocarbon feed and/or the steam feed is supplied into the reaction vessel.

A23. The process of A21 or A22, wherein in the auxiliary furnace, a portion of the $H_2$-rich stream is combusted to provide thermal energy.

A24. The process of any of A1 to A23, wherein the $CO_2$ stream comprises $CO_2$ at a concentration of no less than 90 mol %, based on the total moles of molecules in the $CO_2$ stream.

A25. The process of any of A1 to A24, wherein the $CO_2$ stream comprises at least one preferably all of: no greater than 5 mol % of CO; no greater than 6 mol % of $H_2O$; no greater than 5 mol % of $CH_4$.

A26. The process of any of A1 to A25, further comprising at least one of the following:

conducting away at least a portion of the $CO_2$ stream produced in step (VII) in a pipeline;

storing at least a portion of the $CO_2$ stream in a geological formation;

using at least a portion of the $CO_2$ stream in extracting hydrocarbons present in a geological formation; and using at least a portion of the $CO_2$ stream in food applications.

A27. The process of any of A1 to A26, wherein step (VIII) comprises combusting a portion of the $H_2$-rich stream in a steam cracker located in an olefins production plant and operated under steam cracking conditions to convert a steam cracker feed into a steam cracker effluent comprising olefins.

A28. The process of A27, wherein the steam cracker is equipped with a combustion air preheater to reduce the fuel consumption requirements of the steam cracker.

A29. The process of A28, wherein step (VIII) further comprises combusting a portion of the $H_2$-rich stream in a boiler located in the olefins production plant to generate steam.

A30. The process of any of A27 to A29, wherein the olefins production plant comprises a combined-cycle power plant, the combined-cycle power plant comprises one or more duct burners combusting a duct burner fuel to generate thermal energy, and step (VIII) further comprises combusting a portion of the $H_2$-rich stream as at least a portion of the duct burner fuel.

A31. The process of any of A1 to A30, wherein the hydrocarbon feed comprises natural gas.

A32. The process of A1 to A31, wherein the $CH_4$-rich stream comprises $CH_4$ at a concentration of no less than 50 mol % (preferably ≥75 mol %, preferably ≥80 mol %, preferably ≥90 mol %), based on the total moles of hydrocarbons in the $CH_4$-rich stream.

A33. The process of A32, wherein the $CH_4$-rich stream comprises at least one preferably all of: ≤40 mol % $H_2$; ≤10 mol % ethane; and <5 mol % CO, based on the total moles of molecules in the $CH_4$-rich stream.

A34. The process of A32 or A33, wherein the $CH_4$-rich stream has an absolute pressure higher than that of the hydrocarbon feed supplied into the syngas producing unit in step (I).

A35. The process of A34, further comprising:

(XIV) expanding the $CH_4$-rich stream through a turbo-expander and/or a Joule-Thompson valve to produce a cooled $CH_4$-rich stream having a pressure in the vicinity of the pressure of the hydrocarbon feed; and (XV) heating the cooled $CH_4$-rich stream by using a stream in the olefins production plant via a heat exchanger.

A36. The process of any of A32 to A34, wherein the CH$_4$-rich stream has an absolute pressure lower than that of the hydrocarbon feed supplied into the syngas producing unit in step (I), and the process further comprises:

(XVI) compressing the CH$_4$-rich stream to a pressure in the vicinity of the pressure of the hydrocarbon feed.

A37. The process of any of A27 to A37, further comprising:

(XVII) producing a steam-cracker H$_2$ stream from the steam cracker effluent; and (XVIII) combining the H$_2$-rich stream and at least a portion of the steam-cracker H$_2$ stream to form a fuel-gas stream.

A38. The process of A37, further comprising:

(XIX) combusting a portion of the fuel-gas stream in at least one of the following: the steam cracker; the plurality of duct burners; the boilers; an ATR auxiliary furnace; and an SMR auxiliary furnace.

A39. The process of A37 or A38, wherein the steam-cracker H$_2$ stream comprises ≥80 mol % of H$_2$, based on the total moles of molecules in the steam-cracker H$_2$ stream.

A40. The process of any of A37 to A39, wherein the H$_2$-rich stream and the steam-cracker H$_2$ stream together provides at least 60%, on a BTU basis, of the total combustion fuel needed by the operation of the olefins production plant.

B1. A process comprising:

(i) supplying a hydrocarbon feed and a steam feed into a syngas producing unit comprising a reforming reactor under syngas producing conditions to produce a reformed stream exiting the reforming reactor, wherein the syngas producing conditions include the presence of a reforming catalyst, and the reformed stream comprises H$_2$, CO, and steam;

(ii) cooling the reformed stream by using a waste heat recovery unit ("WHRU") to produce a cooled reformed stream and to generate a high-pressure steam ("HPS") stream;

(iii) contacting the cooled reformed stream with a first shifting catalyst in a first shift reactor under a first set of shifting conditions to produce a first shifted stream exiting the first shift reactor, wherein the first shifted stream has a lower CO concentration and a higher CO$_2$ concentration than the cooled reformed stream;

(iv) cooling the first shifted stream to obtain a cooled first shifted stream;

(v) contacting the cooled first shifted stream with a second shifting catalyst in a second shift reactor under a second set of shifting conditions to produce a second shifted stream exiting the second shift reactor, wherein the second shifted stream has a lower CO concentration and a higher CO$_2$ concentration than the cooled first shifted stream;

(vi) abating steam present in the second shifted stream to produce a crude gas mixture stream comprising CO$_2$ and H$_2$;

(vii) recovering at least a portion of the CO$_2$ present in the crude gas mixture stream to produce a CO$_2$ stream and a H$_2$-rich stream, wherein the H$_2$-rich stream comprises H$_2$ at a concentration of at least 80 mol %, based on the total moles of molecules in the H$_2$-rich stream; and (viii) combusting a portion of the H$_2$-rich stream in the presence of an oxidant to generate thermal energy and to produce a flue gas stream; where step (VIII) comprises:

(viiia) combusting a portion of the H$_2$-rich stream in a steam cracker located in an olefins production plant to generate thermal energy and to produce a flue gas stream comprising CO$_2$ at a concentration no greater than 20 mol % based on the total moles of H$_2$O and CO$_2$ in the flue gas stream, wherein the steam cracker is operated under steam cracking conditions to convert a steam cracker feed into a steam cracker effluent comprising olefins.

B2. The process of B1, wherein:
the syngas producing unit comprises a SMR;
the SMR comprises: one or more SMR burners where a SMR fuel combusts to supply thermal energy to the SMR; a radiant section heated by the thermal energy in which the hydrocarbon feed and steam reacts under the syngas producing conditions; a convection section heated by the thermal energy in which the hydrocarbon feed and steam are preheated before entering the radiant section; and step (viii) further comprises:

(viiib) combusting a portion of the H$_2$-rich stream at the plurality of SMR burners as at least a portion of the SMR fuel.

B3. The process of B for B2, further comprising:

(ix) producing a CH$_4$-rich stream from the steam cracker effluent; and (x) providing the CH$_4$-rich stream as at least a portion of the hydrocarbon feed.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process comprising:

(I) supplying a hydrocarbon feed and a steam feed into a syngas producing unit comprising a reforming reactor under syngas producing conditions to produce a reformed stream exiting the reforming reactor, wherein the syngas producing conditions include the presence of a reforming catalyst, and the reformed stream comprises H$_2$, CO, and steam;

(II) cooling the reformed stream by using a waste heat recovery unit ("WHRU") to produce a cooled reformed stream and to generate a high-pressure steam ("HPS") stream;

(III) contacting the cooled reformed stream with a first shifting catalyst in a first shift reactor under a first set of shifting conditions to produce a first shifted stream exiting the first shift reactor, wherein the first shifted stream has a lower CO concentration and a higher CO$_2$ concentration than the cooled reformed stream;

(IV) cooling the first shifted stream to obtain a cooled first shifted stream;

(V) contacting the cooled first shifted stream with a second shifting catalyst in a second shift reactor under a second set of shifting conditions to produce a second shifted stream exiting the second shift reactor, wherein the second shifted stream has a lower CO concentration and a higher CO$_2$ concentration than the cooled first shifted stream;

(VI) abating steam present in the second shifted stream to produce a crude gas mixture stream comprising CO$_2$ and H$_2$;

(VII) recovering at least a portion of the CO$_2$ present in the crude gas mixture stream to produce a CO$_2$ stream and a $H_2$-rich stream, wherein the $H_2$-rich stream comprises $H_2$ at a concentration of at least 80 mol %, based on the total moles of molecules in the $H_2$-rich stream;

(VIII) combusting a portion of the $H_2$-rich stream in the presence of an oxidant to generate thermal energy and to produce a flue gas stream;

(IX) operating a steam cracker located in an olefins production plant under steam cracking conditions to convert a steam cracker feed into a steam cracker effluent comprising olefins;

(X) producing a $CH_4$-rich stream from the steam cracker effluent; and (XI) providing the $CH_4$-rich stream as at least a portion of the hydrocarbon feed in step (I).

2. The process of claim 1, wherein the $H_2$-rich stream further comprises $H_2$ at a concentration of at least 85 mol % and at least one of: ≤5 mol % of $CH_4$; ≤3 mol % CO; and ≤1 mol % $CO_2$, based on the total moles of molecules in the $H_2$-rich stream.

3. The process of claim 1, wherein the reformed stream has at least one of the following: a temperature of from 750° C. to 1,200° C., and an absolute pressure from 700 kPa to 5000 kPa.

4. The process of claim 1, wherein the cooled reformed stream produced in step (II) has a temperature from 285° C. to 400° C.

5. The process of claim 1, wherein the HPS stream generated in step (II) has an absolute pressure from 4,000 kPa to 14,000 kPa, and the process further comprises:

(XII) heating the HPS stream to produce a superheated HPS ("SH-HPS") stream; and (XIII) supplying a portion of the SH-HPS stream to the syngas producing unit as at least a portion of the steam feed.

6. The process of claim 1, wherein in step (III), the first shifted stream has at least one of the following: a temperature from 335° C. to 500° C.; and an absolute pressure from 700 kPa to 5,000 kPa.

7. The process of claim 1, wherein step (IV) comprises cooling the first shifted stream, via a heat exchanger, by a cooling stream selected from: a stream comprising the hydrocarbon feed; a boiler feed water stream; and combinations thereof.

8. The process of claim 1, wherein the cooled first shifted stream has at least one of the following: a temperature from 150° C. to 250° C., and an absolute pressure from 700 kPa to 5,000 kPa.

9. The process of claim 1, wherein in step (V), the second shifted stream has at least one of the following: a temperature from 150° C. to 300° C.; an absolute pressure from 700 kPa to 3500 kPa; and a CO concentration no greater than 5.0 mol %, based on the total moles of molecules in the second shifted stream.

10. The process of claim 1, wherein step (VI) comprises:

(VIa) cooling the second shifted stream to condense a portion of steam in the second shifted stream to form liquid water and to obtain a cooled second shifted stream; and (VIb) separate the liquid water from the cooled second shifted stream to obtain the crude gas mixture stream.

11. The process of claim 1, wherein step (VII) comprises at least one of the following:

(VIIa) separating at least a portion of the crude gas mixture stream by using an amine absorption and regeneration process;

(VIIb) separating at least a portion of the crude gas mixture stream by using a cryogenic $CO_2$ separation process;

(VIIc) separating at least a portion of the crude gas mixture stream by using a membrane separation process; and (VIId) separating at least a portion of the crude gas mixture stream by using a physical absorption and regeneration process.

12. The process of claim 1, wherein the syngas producing unit comprises a steam-methane-reformer ("SMR") and/or an autothermal reformer ("ATR").

13. The process of claim 12, wherein:

the syngas producing unit comprises a SMR;

the SMR comprises: one or more SMR burners where a SMR fuel combusts to supply thermal energy to the SMR; a radiant section heated by the thermal energy in which the hydrocarbon feed and steam react under the syngas producing conditions; a convection section heated by the thermal energy in which the hydrocarbon feed and steam are preheated before entering the radiant section; and in step (VII), a portion of the $H_2$-rich stream is supplied to the plurality of SMR burners as at least a portion of the SMR fuel.

14. The process of claim 13, further comprising:

(XIIa) heating the HPS stream generated in step (II) in the convection section of the SMR and/or an auxiliary furnace to obtain a super-heated HPS ("SH-HPS") stream having at least one of the following: a temperature from 350° C. to 550° C., and a pressure from 4,000 kPa to 14,000 kPa.

15. The process of claim 12, wherein:

the syngas producing unit comprises an ATR;

an $O_2$ stream is fed into the ATR;

the ATR comprises a reaction vessel into which the hydrocarbon feed, the steam feed, and the $O_2$ stream are supplied;

the syngas producing conditions comprises the presence of an ATR catalyst in the reaction vessel; and the reformed stream has at least one of the following: a temperature from 800° C. to 1200° C.; and an absolute pressure from 700 kPa to 5,000 kPa.

16. The process of claim 15, further comprising:

(XIIb) heating the HPS stream generated in step (II) in an auxiliary furnace to obtain a super-heated HPS ("SH-HPS") stream having at least one of the following: a temperature from 350° C. to 550° C., and a pressure from 4,000 kPa to 14,000 kPa.

17. The process of claim 1, wherein step (VIII) comprises combusting a portion of the $H_2$-rich stream in the steam cracker, the olefins production plant optionally produces a steam-cracker $H_2$ stream, and the process further comprises optionally combining a portion of the $H_2$-rich stream with a portion of the steam-cracker $H_2$ stream to form a joint $H_2$-rich stream.

18. The process of claim 17, wherein the process comprises combusting a portion of the $H_2$-rich stream, and/or a portion of the steam-cracker $H_2$ stream, and/or a portion of the joint $H_2$-rich stream in an SMR, a boiler, and/or an auxiliary furnace.

19. The process of claim 17, wherein the olefins production plant comprises a combined-cycle power plant, the combined-cycle power plant comprises one or more duct burners combusting a duct burner fuel to generate thermal energy, and the process further comprises combusting a portion of the $H_2$-rich stream and/or a portion of the steam-cracker H$_2$ stream and/or a portion of the joint H$_2$-rich stream as at least a portion of the duct burner fuel.

20. The process of claim 1, wherein the CH$_4$-rich stream comprises at least one: ≤40 mol % H$_2$; ≤10 mol % ethane; and ≤5 mol % CO, based on the total moles of molecules in the CH$_4$-rich stream.

21. The process of claim 1, wherein the CH$_4$-rich stream has an absolute pressure higher than that of the hydrocarbon feed supplied into the syngas producing unit in step (I), and the process further comprises:
(XIV) expanding the CH$_4$-rich stream through a turbo-expander and/or a Joule-Thompson valve to produce a cooled CH$_4$-rich stream having a pressure in the vicinity of the pressure of the hydrocarbon feed; and
(XV) heating the cooled CH$_4$-rich stream by using a stream in the olefins production plant via a heat exchanger.

22. The process of claim 17, wherein the H$_2$-rich stream and the steam-cracker H$_2$ stream together provides at least 60%, on a BTU basis, of the total combustion fuel needed by the operation of the olefins production plant.

23. The process of claim 22, wherein the H$_2$-rich stream provides at least 60%, on a BTU basis, of the total combustion fuel needed by the operation of the olefins production plant.

24. A process comprising:
(i) supplying a hydrocarbon feed and a steam feed into a syngas producing unit comprising a reforming reactor under syngas producing conditions to produce a reformed stream exiting the reforming reactor, wherein the syngas producing conditions include the presence of a reforming catalyst, and the reformed stream comprises H$_2$, CO, and steam;
(ii) cooling the reformed stream by using a waste heat recovery unit ("WHRU") to produce a cooled reformed stream and to generate a high-pressure steam ("HPS") stream;
(iii) contacting the cooled reformed stream with a first shifting catalyst in a first shift reactor under a first set of shifting conditions to produce a first shifted stream exiting the first shift reactor, wherein the first shifted stream has a lower CO concentration and a higher CO$_2$ concentration than the cooled reformed stream;
(iv) cooling the first shifted stream to obtain a cooled first shifted stream;
(v) contacting the cooled first shifted stream with a second shifting catalyst in a second shift reactor under a second set of shifting conditions to produce a second shifted stream exiting the second shift reactor, wherein the second shifted stream has a lower CO concentration and a higher CO$_2$ concentration than the cooled first shifted stream;
(vi) abating steam present in the second shifted stream to produce a crude gas mixture stream comprising CO$_2$ and H$_2$;
(vii) recovering at least a portion of the CO$_2$ present in the crude gas mixture stream to produce a CO$_2$ stream and a H$_2$-rich stream, wherein the H$_2$-rich stream comprises H$_2$ at a concentration of at least 80 mol %, based on the total moles of molecules in the H$_2$-rich stream;
(viii) combusting a portion of the H$_2$-rich stream in the presence of an oxidant to generate thermal energy and to produce a flue gas stream; where step (VIII) comprises:
(viiia) combusting a portion of the H$_2$-rich stream in a steam cracker located in an olefins production plant to generate thermal energy and to produce a flue gas stream comprising CO$_2$ at a concentration no greater than 20 mol % based on the total moles of H$_2$O and CO$_2$ in the flue gas stream, wherein the steam cracker is operated under steam cracking conditions to convert a steam cracker feed into a steam cracker effluent comprising olefins;
(ix) producing a CH$_4$-rich stream from the steam cracker effluent; and
(x) providing the CH$_4$-rich stream as at least a portion of the hydrocarbon feed.

25. The process of claim 24, wherein:
the syngas producing unit comprises a SMR;
the SMR comprises: one or more SMR burners where a SMR fuel combusts to supply thermal energy to the SMR; a radiant section heated by the thermal energy in which the hydrocarbon feed and steam reacts under the syngas producing conditions; a convection section heated by the thermal energy in which the hydrocarbon feed and steam are preheated before entering the radiant section; and step (viii) further comprises:
(viiib) combusting a portion of the H$_2$-rich stream at the plurality of SMR burners as at least a portion of the SMR fuel.

* * * * *